US 6,635,281 B2

(12) United States Patent
Wong et al.

(10) Patent No.: US 6,635,281 B2
(45) Date of Patent: Oct. 21, 2003

(54) GASTRIC RETAINING ORAL LIQUID DOSAGE FORM

(75) Inventors: Patrick S.-L. Wong, Burlingame, CA (US); David E. Edgren, Los Altos, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 09/469,656

(22) Filed: Dec. 22, 1999

(65) Prior Publication Data

US 2003/0017189 A1 Jan. 23, 2003

Related U.S. Application Data

(60) Provisional application No. 60/113,615, filed on Dec. 23, 1998.

(51) Int. Cl.[7] .............................. A61K 9/26; A61K 9/22; A61K 9/24
(52) U.S. Cl. ........................ 424/473; 424/426; 424/464; 424/468; 424/469; 514/772.4; 514/781; 514/770
(58) Field of Search .................. 424/602, 683, 424/688, 468, 426, 469, 473, 480, 489, 494, 498, 464; 514/781, 772.4

(56) References Cited

U.S. PATENT DOCUMENTS

| | | | |
|---|---|---|---|
| 2,707,154 A | 4/1955 | Lehmann et al. ............. 99/163 |
| 2,805,977 A | 9/1957 | Robinson et al. ............. 167/82 |
| 3,637,772 A | 1/1972 | Klaui et al. ............... 260/398.5 |
| 4,038,434 A | 7/1977 | Young ........................ 426/544 |
| 4,182,330 A | 1/1980 | Michaels .................... 128/260 |
| 4,186,465 A | 2/1980 | Manning ............... 24/201 HH |
| 4,259,323 A | 3/1981 | Ranucci ...................... 424/153 |
| 4,290,426 A | 9/1981 | Luschen et al. ............. 128/260 |
| 4,559,237 A | 12/1985 | Meier et al. ................ 427/53.1 |
| 4,767,627 A | 8/1988 | Caldwell et al. ............. 424/426 |
| 4,839,177 A | 6/1989 | Colombo et al. ............ 424/482 |
| 4,851,232 A | 7/1989 | Urquhart et al. ............ 424/469 |
| 4,871,548 A | 10/1989 | Edgren et al. .............. 424/488 |
| 4,931,285 A | 6/1990 | Edgren et al. .............. 424/473 |
| 5,007,790 A | 4/1991 | Shell .......................... 424/451 |
| 5,024,842 A | 6/1991 | Edgren et al. .............. 424/473 |
| 5,112,817 A | 5/1992 | Fukazawa et al. .......... 514/183 |
| 5,256,440 A | 10/1993 | Appel et al. .................... 427/3 |

(List continued on next page.)

OTHER PUBLICATIONS

Van Nostrand Reinhold Encyclopedia of Chemistry 4th ed. Considine and Considine, eds., 644–645 (1984).

(List continued on next page.)

Primary Examiner—James M. Spear
Assistant Examiner—Liliana Di Nola-Baron
(74) Attorney, Agent, or Firm—Samuel E. Webb

(57) ABSTRACT

The present invention is directed to an active agent dosage form which is adapted for retention in the stomach and useful for the prolonged delivery of a liquid, active agent formulation to a fluid environment of use. The liquid, active agent formulation is sorbed into porous particles that are dispersed in a polymer matrix that swells upon contact with the fluids of the stomach. A portion of the polymer matrix may be surrounded by a band of insoluble material that prevents the covered portion of the polymer matrix from swelling and provides a segment of the dosage form that is of sufficient rigidity to withstand the contractions of the stomach and delay expulsion of the dosage form from the stomach until substantially all of the active agent has been dispensed.

9 Claims, 4 Drawing Sheets

U.S. PATENT DOCUMENTS

| | | | | |
|---|---|---|---|---|
| 5,389,380 A | * | 2/1995 | Noda et al. | 424/490 |
| 5,443,843 A | | 8/1995 | Curatolo et al. | 424/464 |
| 5,486,365 A | | 1/1996 | Takado et al. | 424/602 |
| 5,534,263 A | | 7/1996 | Wong et al. | 424/473 |
| 5,582,837 A | | 12/1996 | Shell | 424/451 |
| 5,643,909 A | | 7/1997 | Pfister et al. | 514/253 |
| 5,707,649 A | * | 1/1998 | Inokuchi et al. | 424/450 |
| 5,780,057 A | | 7/1998 | Conte et al. | 424/468 |
| 5,800,834 A | | 9/1998 | Spireas et al. | 424/451 |
| 5,824,638 A | | 10/1998 | Burnside et al. | 514/3 |
| 6,120,803 A | * | 9/2000 | Wong et al. | 424/473 |

OTHER PUBLICATIONS

Pharmaceutical Sciences 17th ed. by Remington, 403–405 (1985).

Br. J. Clin. Pharmac. 21:459–462(1968) Lewis et al. Human gastrointestinal absorption of acyclovir from tablet duodenal infusion and sipped solution.

Journal of Controlled Release 26:39–47(1993) Conte et al. Multi–layered hydrophilic matrices as constant release devices (Geomatrix TM Systems).

International Journal of Pharmaceutics 62:R9–R11 (1990) Khosla et al. The effect of tablet size on the gastric emptying of non–disintegrating tablets.

Pharmaceutical Research 8(10): 1281–1285 (1991) Coupe et al. Correlation of the gastric emptying of nondisintegrating tablets with gastrointestinal motility.

Drug Development and Industrial Pharmacy 16(5):769–777 (1990) Sheth et al. Use of powdered solutions to improve the dissolution rate of polythiazide tablets.

Journal of Controlled Release 19:131–144 (1992) Shalaby et al. In vitro and in vivo studies of enzyme–digestible hydrogels for oral drug delivery.

Journal of Pharmaceutical Sciences 82(8):854 (1993) The cutoff size for gastric emptying of dosage forms.

International Journal of Pharmaceutics 38:221–225 (1987) Wilson et al. The influence of food on the absorption of acyclovir: . . .

The United States Pharmacopeia 23/The National Formulary 18:1791–1796 (1995).

Journal of Pharmaceutical Sciences 66(1):1–19 (1977).

Fuji Chemical Industry Co., Ltd., Fujicalin product information.

Fuji Chemical Industry Co., Ltd., Material Safety Data Sheet.

Fuji Chemical Industry Co., Ltd., Physico–Chemical Properties of Neusilin.

Fuji Chimical Industry Co., Ltd, "Neusilin UFL2,".

Fuji Chemical Industries (USA) Inc., "Neusilin The Extraordinary Excipient," Fuji Chemical Industries (USA) Inc.

Fuji Chemical Industry Co., Ltd, "Creation and Service,".

* cited by examiner

GASTRIC RETAINING ORAL LIQUID DOSAGE FORM

This application claims the priority of provisional application No. 60/113,615, filed Dec. 23, 1998, which is incorporated herein by reference.

FIELD OF THE INVENTION

The present invention is related to the prolonged release of an active agent from a dosage form. More particularly, it relates to a dosage form, containing a liquid, active agent formulation, the dosage form being adapted to be retained in the stomach for a prolonged period of time, during which a liquid, active agent formulation is released to the environment of use.

BACKGROUND OF THE INVENTION

Controlled release dosage forms that provide for prolonged delivery of active agent formulations to the environment of use have found application for increasing numbers of active agents. However, it has generally been a problem to deliver liquid, active agent formulations to the stomach of a subject continuously or intermittently over a prolonged period of time. Particularly when the active agent is absorbed only in the upper gastrointestinal tract, the bioavailability of the active agent may be greatly reduced if it is rapidly released from the stomach and passes quickly through the upper gastrointestinal tract. The period of time for absorption may be too short for an effective amount of active agent to be absorbed over a reasonable period of time, without frequent, subsequent dosing. This is particularly a problem with liquid forms of active agents, since they tend not to be retained within the stomach for more than a short period of time. Instead they tend to pass quickly from the stomach, through the upper gastrointestinal tract and into the lower gastrointestinal tract.

Generally, the time of passage of different particles through the small intestine does not vary significantly, and passage is generally independent of food intake and particle size. Thus, active agent dissolved in liquid, solid active agent dispersed in liquid and relatively larger delivery units of active agent, such as microcapsules and the like, will traverse the length of the small intestine in substantially the same time frame, usually about 3–5 hours. However, if liquid active agents can be retained in the stomach and released over a prolonged period of time, the active agent can be delivered to the small intestine over a time much longer than the 3–5 hour window, increasing the likelihood of increased absorption.

Most active agents are not well absorbed in the stomach, but even in those instances where the active agent is not well absorbed, the continuous release of active agent in the stomach over a prolonged time period will dispense active agent over that same period of time to the small intestine where it can be absorbed.

The physiological behavior of the stomach is usually determined by whether it contains food or is empty. Food is mixed and partially digested in the distal stomach (antrum). As the stomach undergoes contractions, partially digested material is discharged into the small intestine and non-digested material is retropelled into the main part of the stomach for further digestion. In the fed state, non-digestible material is not generally able to leave the stomach. At the end of a digestive period, the stomach enters the fasting stage and begins a cycle called the interdigestive myoelectric motor cycle or IMMC.

The IMMC can be considered to be divided into four phases: (1) phase 1 is an approximately one hour period with no contractions; (2) phase 2 is about a forty minute period of intermittent potentials and contractions that increase in intensity over time; (3) phase 3 is a relatively short period, generally between about five to fifteen minutes, of intense contractions (commonly called the "housekeeper wave") that completely empties the stomach; and (4) phase 4 is a short transitory period between the intense activity of phase 3 and the quiescence of phase 1. The different phases move distally from the stomach to the terminal ileum over an approximately two hour period as the cycle is repeated. Since the cycle is interrupted by the receipt of food by the stomach, it is possible to delay the emptying phase, phase 3, by maintaining a fed state. However, it is not practical to regularly maintain the fed state over a long period of time. Consequently, a need exists for a delivery device that can remain in the stomach for a significant period, whether in the fed or fasted state, and deliver active agent to the stomach over a prolonged period of time.

A variety of studies have been conducted in dog and in man to determine sizes of objects that would be retained in the stomach during the fed stage and also in the fasting stage when IMMC is present. Khosla and Davis, *International Journal of Pharmaceutics*, Vol. 62 (1990), pages R9–R11 have reported that a particle size less that 2 mm generally results in emptying from the stomach of the dog. Non-disintegrating tablets having sizes of 7, 11 and 13 mm in diameter were emptied from the human stomach, but the larger sized tablets tended to remain in the stomach longer than the small sized tablets. Tablets larger than 11 mm tended to be emptied only during the IMMC. Davis et al., *Pharmaceutical Research*, Vol. 8, No. 10 (1991) has described retention of radio-telemetry capsules having a size of 25×8 mm in the stomach of human subjects past phase 3 of the IMMC. Timmermans et al., *Journal of Pharmaceutical Sciences*, Vol. 82, No. 8 (1993) has reported the mean resting pyloric diameter in humans as 12.8±7.0 mm. Accordingly, it is important that gastric retentive delivery vehicles are adapted to disintegrate, dissolve or erode to sizes that permit eventual elimination of the vehicle without causing gastric obstruction.

The influence of food on gastric retention time and the absorption of acyclovir has been reported in *International Journal of Pharmaceutics*, Vol. 38 (1987), pages 221–225. As reported there, compared to a lighter meal, the heavier meal slowed the rate of gastric emptying, prolonged small intestinal transit time and decreased absorption of the active agent.

Various attempts to provide active agent delivery devices that remain in the stomach for extended periods or time have been described previously. For example, U.S. Pat. No. 4,851,232 describes a hydrogel reservoir containing tiny pills having a active agent core surrounded by a wall controlling delivery of active agent to the stomach. The hydrogel swells in the stomach to facilitate retention of the active agent reservoir in the stomach over time.

U.S. Pat. No. 4,871,548 describes a dosage form including a mixture of low and high number average molecular weight hydroxypropyl methylcellulose polymers and active agent that swells when in the stomach.

U.S. Pat. No. 4,767,627 describes substantially planar devices formed of bioerodible polymer including active agent that may be compressed and folded for oral administration and then released and unfolded in the stomach, where the devices are to be retained over an extended period of time. The devices have a longest diameter of between 1.6 and 5 cm. It is suggested that as an alternative to incorporating the active agent into the device a controlled release active agent module, mechanically or osmotically driven, can be glued or tethered to the device.

U.S. Pat. No. 5,443,843 describes a plurality of compressible retention arms and an attached controlled release device which in the expanded form resists gastrointestinal transit. The system can have a collar or a belt for receiving and holding a active agent-containing, orally-administrable controlled release device. In a fully expanded configuration for human use, the system is described as having minimum and maximum dimensions of 2.5 and 6.0 centimeters, respectively.

U.S. Pat. No. 5,007,790 describes a sustained release active agent dosage form in the form of a capsule or tablet that includes a plurality of hydrophilic water-swellable, cross-linked polymer particles that swell in the stomach to promote gastric retention and permit gastric fluid to penetrate the particles to dissolve active agent and deliver it to the stomach in the solution state. The particles are indicated to retain their physical integrity over the dosing period. Initially sized particles, indicated to be preferably spherical, are disclosed to be in the range of 50 $\mu$m to 2 mm, swell to a size of about 3 mm. A plurality of particles are packed into a capsule for administration to a patient.

U.S. Pat. No. 5,582,837 describes a dosage form similar to that of U.S. Pat. No. 5,007,790, without the use of a cross-linked hydrophilic polymer. The particles are described as slippery and soft, preferably spherical, and having dimensions on the order of 6 to 18 mm in the swollen state. The particles can be packed into capsules containing 7–25 spherical particles, depending on the size, or formulated into tablets that contain from 2–25 spherical particles.

The use of albumin-cross-linked polyvinylpyrrolidone hydrogels to deliver flavin mononucleotide to dogs has been described by Park et al. in *Journal of Controlled Release*, Vol. 19 (1992) pages 131–134. The hydrogels were maintained in the stomachs of dogs for extended periods, even in the fasted state. Gels with a glassy core tended to remain in the stomach longer than hydrogels without the glassy core. Control of the size of the core was attempted by administration of water in the stomach. While it is possible to control the dimensions of the hydrogel in the dry state, controlling the size of the glassy core within the hydrogel after administration to a subject by addition of water is not suitable for fabrication of a dosage form that can routinely and controllably be retained in the stomach of a subject over a prolonged period of time.

While it is important that the delivery device be adapted to remain in the stomach for a prolonged period, it is also important that the device deliver active agent in a controlled manner. Delivery systems, such as those described below, are representative of the many different systems have been suggested for such controlled delivery of active agents over a prolonged period of time.

For example, U.S. Pat. No. 4,290,426 to Lusted et al describes a cylindrical dispenser for releasing a beneficial agent into a fluid environment at a rate that is governed by the fluid induced relaxation of a polymeric agent contained within the dispenser. The cylindrical dispenser includes an impermeable container that has within it a reservoir and a passageway from the reservoir to the exterior of the container. The reservoir contains a polymer and a beneficial agent. The polymer imbibes fluid from the environment and thereby undergoes relaxation, releasing the beneficial agent from the device. The amount of agent released is dependent on the rate of relaxation of the polymer over time.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage form core surface. The remainder of the film remains attached to the dosage form core. The exposed portion of the dosage form surface erodes and releases active agent to the environment of use.

Coated tablets for constant and prolonged active agent release are described by Conte et al in *J. Controlled Release*, Vol. 26, (1993) pages 39–47. These GEOMATRIX™ Systems are swellable matrices that are coated or tableted with polymeric barrier layers. Release performances of the systems are modulated as a result of the reduction of the releasing surface exposed to the dissolution medium by the polymeric barrier layer coatings. As the extent of coating of the system's surface is increased, the release kinetics of the system shift toward constant release. These systems are further described in U.S. Pat. No. 4,839,177 to Colombo et al.

U.S. Pat. No. 5,534,263, which is incorporated herein by reference, describes a dosage form useful for the prolonged delivery of an active agent formulation in the form of a matrix having two or more insoluble bands on the surface of the matrix. The exposed surfaces of the matrix erode in a manner that creates additional surface areas to provide for prolonged release of an active agent formulation with determined release profiles.

A layered tablet wherein at least one layer can swell by contact with biological fluids to prolong residence at the gastric level is described in U.S. Pat. No. 5,780,057.

Generally the foregoing systems have been directed to the delivery of active agents which are in the dosage forms initially in the dry state. Little effort appears to have been made to deliver liquid active agent formulations that would be retained in the stomach for a sustained period of time.

Administration of acyclovir by sipped solution over a four-hour period has been described in *Br. J. clin. Pharmac.*, 21, 459–462 (1986) to achieve an increased contact time with the human stomach and the gastrointestinal tract. The total amount of acyclovir absorbed was increased over that observed with administration of acyclovir tablets. However, no attempt was made to maintain the acyclovir solution in the stomach for a sustained period except by continuous oral administration. Obviously, continuous oral administration is not a reasonable solution to the general problem of maintaining liquid active agent in the stomach for a sustained period of time.

Furthermore, when the active agent is insoluble or poorly soluble, prior art systems may not provide suitable delivery of active agent or concentration gradients at the site of absorption for that period of time that the active agent sees the absorption site. Various attempts have been made to address such problems, including the use of water-soluble salts, self-emulsifying compositions, polymorphic forms, powdered solutions, molecular complexes, micronization, eutectics, and solid solutions, in the context of immediate release delivery. An example of the use of a powdered solution is described by Sheth, et al., in "Use of Powdered Solutions to Improve the Dissolution Rate of Polythiazide Tablets," Drug Development and Industrial Pharmacy, 16(5), 769–777 (1990). References to certain of the other approaches are cited therein. Additional examples of powdered solutions are described in U.S. Pat. No. 5,800,834. The patent describes methodology for calculating the amount of liquid that may be optimally sorbed into materials to prevent the drug solution from being exuded from the granular composition during compression.

U.S. Pat. No. 5,486,365, which is incorporated herein by reference, describes a spheronized material formed from a scale-like calcium hydrogen phosphate particulate material having a high specific surface area, good compressibility and low friability. That patent indicates that the material has the characteristic of high liquid absorption. However, the patent does not suggest that the material may be used as a carrier for delivery of a liquid medicament formulation to the environment of use. Instead, the patent describes the formation of a dried formulation, such as formed by spray drying. The patent describes the use of a suspension containing medicines and binders during the spray-drying granulation process to form a spherical particle containing the medicine. As an example, ascorbic acid in an amount equivalent to 10% of the scale-like calcium hydrogen phosphate was dissolved into a slurry of 20 weight percent of calcium hydrogen phosphate in water, and the resulting slurry was spray dried to form dried, spherical calcium hydrogen phosphate containing ascorbic acid. That material was then tableted under loads of 500–2000 kg/cm$^2$.

SUMMARY OF THE INVENTION

As can be observed in the above-referenced patents and publications, devices have been described that provide for prolonged delivery of an active agent and retention in the gastric environment. However, there remains a continuing need for improved systems for delivering a liquid, active agent formulation to the gastric environment over a prolonged period of time and in a reliable, controllable and reproducible manner. In particular, there is a need for controlled release delivery devices that are to remain in the stomach, even during a fasting state in which IMMC is present, for a prolonged period, for example from about 3 hours to up to about 20–24 hours, and deliver a liquid, active agent formulation. Such devices should exhibit a combination of flexibility and rigidity so as not to be expelled from the stomach into the pyloric sphincter under fed or fasting conditions, and deliver active agent in a reproducible, controlled manner, over a prolonged period of time. One such device for delivering solid and liquid active agents has been described in our U.S. Pat. No. 6,120,803 pending U.S. application Ser. No. 09/131,923, filed Aug. 10, 1998, which is incorporated herein by reference.

Accordingly, the present invention is directed to a dosage form that will provide increased retention time of the device in the stomach over conventional dosage forms and release a liquid, active agent formulation in a reliably controllable manner, and further that is easy and inexpensive to manufacture.

In its broadest aspect, the invention comprises a dosage form having a liquid, active agent formulation absorbed in porous particles, the porous particles being dispersed in a bioerodible carrier adapted to be retained within the stomach of a subject for a prolonged period of time. Preferably, the porous particles exhibit low friability so as to resist compaction forces encountered during fabrication of the dosage form.

In another aspect, the invention comprises a dosage form having a liquid, active agent formulation absorbed in porous particles, the porous particles being dispersed in a bioerodible carrier that swells upon imbibing fluid from stomach so as to be retained within the stomach of a subject for a prolonged period of time.

In another aspect, the dosage form comprises a liquid, active agent formulation absorbed in porous particles, the porous particles being adapted to resist compaction forces sufficient to form a compacted layer without significant exudation of the liquid, active agent formulation admixed with a polymer matrix formed of a mixture of a swellable, water soluble polymer that expands when in contact with fluids in the gastric environment and a hydroattractant, preferably water insoluble. The matrix is formed with a rigid or semi-rigid segment in which swelling of the hydrogel is constrained to provide a rigid or semi-rigid section in the dosage form that facilitates the dosage form remaining in the stomach of a subject over a prolonged period of time. The liquid, active agent formulation is contained in porous particles having high porosity and superior resistance to compressive forces during fabrication of dosage form. In one embodiment, the rigid or semi-rigid section of the dosage form comprises one or more insoluble materials, typically exhibiting low water impermeability and formed as a band circumscribing a portion of the surface of the matrix, that along with the banded portion of the polymer matrix forms the rigid or semi-rigid segment of the dosage form.

The aforementioned insoluble material or band (or bands, if more than one band is utilized) prolongs the period of time in which the polymer matrix retains its integrity in an expanded state and increases the residence time of the dosage form in the stomach. As the dosage form erodes in the stomach or as active agent diffuses from the matrix, the porous particles containing the liquid, active agent formulation will be released over a prolonged period of time, and subsequently the active agent will be either absorbed by the stomach or passed from the stomach to the small intestine where it can be absorbed.

In still another aspect, the active agent dosage form comprises (a) a therapeutically-effective amount of a liquid, active agent formulation sorbed into a porous particle, (b) a polymer matrix in which the porous particle is dispersed, the polymer matrix including a high molecular weight, water-soluble polymer and a hydroattractant such as a water-insoluble polymer, and, optionally, non-polymeric water-soluble excipients and polymers of molecular weight of less than 10,000 grams per mole, the polymer matrix having an outer surface for exposure to the environment of use, and (c) at least one band of insoluble material circumscribing a portion of the outer surface of the polymer matrix.

In still another aspect, the invention comprises a dosage form adapted for gastric retention and delivery of a liquid, active agent formulation over a prolonged period comprising a polymer matrix formed of a water soluble, high molecular weight polymer and a hydroattractant in which the weight percent of the water soluble, high molecular weight polymer is about 10 to 50 weight percent and the weight percent of the hydroattractant is about 5 to 70 weight percent, and a plurality of porous particles containing the liquid, active agent formulation dispersed throughout the polymer matrix.

In a further aspect of the invention, the active agent dosage form comprises a unitary compressed dispersion of a liquid, active agent formulation in a plurality of porous particles in a gel-forming, erodible polymer matrix having a first portion that swells in the stomach while maintaining its physical integrity for a prolonged period of time and a second, non-erodible, non-gel-forming portion for promoting retention of the dosage form in the stomach over a prolonged period of time.

In yet another aspect, the invention comprises a dosage form having a liquid, active agent formulation absorbed in porous particles, the porous particles being dispersed in a bioerodible carrier adapted to be retained within the stomach of a subject for a prolonged period of time, the porous particles being selected from the group consisting of (i) particles, having a mean particle size of 50–150 microns, formed by spray drying a scale-like calcium hydrogen phosphate, having a specific surface area of 20 m$^2$/g to 60 m$^2$/g, an apparent specific volume of 1.5 ml/g or more, an oil absorption capacity of 0.7 ml/g or more, a primary particle size of 0.1$\mu$ to 5$\mu$, and an average particle size of 2$\mu$ to 1$\mu$ among secondary particles that are aggregates of the primary particles, the scale-like calcium hydrogen phosphate being represented by the following general formula:

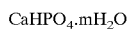

$$CaHPO_4.mH_2O$$

wherein m satisfies the relationship 0≦m≦2.0, and (ii) particles of magnesium aluminometasilicate represented by the general formula

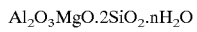

$$Al_2O_3MgO.2SiO_2.nH_2O$$

wherein n satisfies the relationship 0≦n≦10 and having a specific surface area of about 100–300 m$^2$/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g.

In another aspect, the invention comprises a dosage form having a liquid, active agent formulation absorbed in porous particles, the porous particles being dispersed in a bioerodible carrier adapted to be retained within the stomach of a subject for a prolonged period of time, the porous particles being calcium hydrogen phosphate having a specific volume of at least 1.5 ml/g, a BET specific surface area of at least 20 m$^2$/g, and a water absorption capacity of at least 0.7 ml/g. Preferably, the particles have a bulk density of 0.4–0.6 g/ml, a BET surface area of 30–50 m$^2$/g, a specific volume of greater than 2 ml/g, and a mean pore size of at least 50 Angstroms.

In still another aspect, the invention comprises a dosage form having a liquid, active agent formulation absorbed in porous particles, the porous particles being dispersed in a bioerodible carrier adapted to be retained within the stomach of a subject for a prolonged period of time, the porous particles being calcium hydrogen phosphate having a specific volume of at least 1.5 ml/g, a BET specific area of at least 20 m$^2$/g, and a water absorption capacity of at least 0.7 ml/g, the particles having a size distribution of 100% less than 40 mesh, 50%–100% less than 100 mesh and 10%–60% less than 200 mesh. Preferably, 100% is less than 40 mesh, 60%–90% is less than 100 mesh and 20%–60% is less than 200 mesh.

In another aspect, the invention comprises a dosage form having a liquid, active agent formulation absorbed in porous particles, the porous particles being dispersed in a bioerodible carrier adapted to be retained within the stomach of a subject for a prolonged period of time, the porous particles being calcium hydrogen phosphate having a bulk specific volume of 1.5 ml/g–5 ml/g, a BET specific area of 20 m$^2$/g–60 m$^2$/g, a water absorption capacity of at least 0.7 ml/g, and a mean particle size of at least 70 micrometers.

In another aspect, the dosage forms of the invention described above may comprise a gastric-emptying delaying agent, i.e., a substance that increases the retention time of the dosage form in the stomach. The gastric-emptying delaying agent may be combined with the composition containing the active agent for local delivery to the environment of use or it may be coated on the dosage form to provide the desired physiological response to delay onset of the IMMC and facilitate retention of the dosage form in the stomach.

BRIEF DESCRIPTION OF THE DRAWINGS

The figures are not drawn to scale, but are set forth to illustrate various embodiments of the invention. Like numbers refer to like structures.

FIG. 1C illustrating a porous particle having liquid, active agent sorbed therein.

DETAILED DESCRIPTION OF THE INVENTION

Figure 1A:
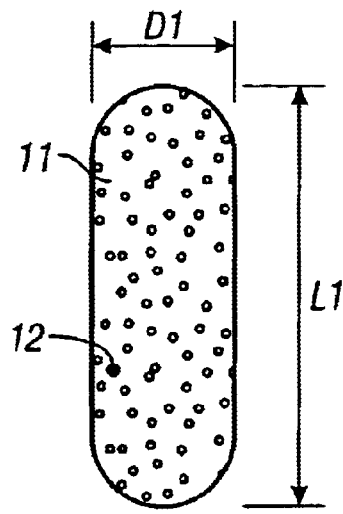
FIGS. 1A, 1B and 1C illustrate one embodiment of the delivery device of the present invention; the device in FIG. 1A representing the active agent formulation matrix not including the insoluble material or band, the device in FIG. 1B representing the banded device in prepared form prior to placement in the stomach.

The present invention provides a dosage form that is retained in the stomach for a prolonged period of time and that is useful for the prolonged delivery of a liquid, active agent formulation to a fluid environment of use. The invention provides for initial and substantially complete delivery of a liquid, active agent formulation in the stomach of a user, where the active agent may be absorbed or released from the stomach to be absorbed in the gastrointestinal tract. In particular applications the gastric retentive dosage forms of the invention may allow for less frequent dosing of the active agent than with immediate release formulations or sustained release formulations that are not gastric retentive dosage forms. In other applications the frequency of dosing may be the same, but the gastric retentive dosage forms will beneficially alter the absorption profile of the active agent from that available with immediate release formulations. This may result in increased bioavailability of the active agent or reduced side effects, for example.

Definitions

The phrase "prolonged period" or "prolonged period of time" intends a time period that lasts for several hours to about 24 hours, usually up to about 12 hours, and often between about 3 and 14 hours, and most often at least 6 hours.

The phrase "prolonged delivery" intends a duration of delivery extending over a time period that lasts for several hours to about 24 hours, usually up to about 12 hours, and often between about 3 and 14 hours, and most often at least 6 hours.

By "insoluble" is intended a material that will not substantially dissolve in the environment of use during the delivery period.

The term "active agent" refers to an agent, drug, compound or other substance, or compositions and mixtures thereof, that provide some pharmacologic, often beneficial, effect. Reference to a specific active agent shall include where appropriate the active agent and its pharmaceutically acceptable salts and may include mixtures of active agents.

The term "polymer matrix" as used herein means a mixture of a water soluble, high molecular weight polymer and a hydroattractant.

The term "liquid, active agent formulation" intends a solution, suspension or dispersion of the active agent or the active agent optionally in combination with pharmaceutically acceptable carriers and additional inert ingredients, in a liquid.

The terms "adapted for gastric retention" or "gastric retentive" mean, with respect to the dosage form of this invention, that the dosage form will remain in the stomach of a subject for a prolonged period of time.

The terms "rigid" and "semi-rigid" mean, with respect to a portion of the active agent formulation matrix or polymer matrix as defined above, that such portion will not swell and form a gel when initially contacted with gastric fluid.

The term "bioerodible" intends a material that will, at least in part, dissolve, degrade or erode in the fluid environment of use.

The term "bioequivalent" intends, with respect to an active agent dosage form of this invention, that there is greater than a 90% probability that the bioavailability of the active agent as determined by standard methods is 80–125% of the defined dosage form and that there is greater than a 90% probability that the maximum blood plasma concentration and the minimum blood plasma concentration of the active agent as measured by standard methods is 80–125% of the defined dosage form.

The term "polymer" means a material formed from a single polymer or a mixture of polymers.

The term "swellable" means, with respect to a polymer or a polymer matrix, that the polymer or polymer matrix is capable of imbibing fluid and expanding when in contact with fluid present in the environment of use.

The terms "therapeutically effective" amount or rate refer to the amount or rate of the active agent needed to effect the desired pharmacologic, often beneficial, result.

The dosage forms of the invention find use, for example, in humans or other animals. The environment of use is a fluid environment and for the purposes of this invention primarily includes the fluid environment of the stomach and the upper intestinal tract or small intestine. A single dosage form or several dosage forms can be administered to a subject during a therapeutic program.

Figure 1B:
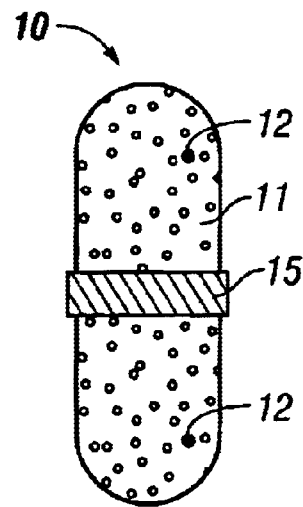
Figure 1C:
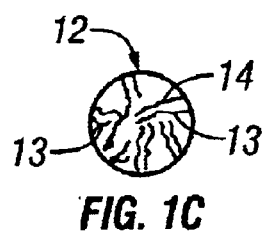

The invention will be better understood with reference to the drawings and the description herein. FIG. 1 depicts one embodiment of the delivery device 10 according to the present invention. The delivery device or active agent dosage form 10 comprises a polymer matrix 11 having a plurality of porous particles 12 having pores 13 in which the liquid, active agent 14 is absorbed (illustrated by the multitude of dots) dissolved or dispersed therein. Polymer matrix 11 typically is formed of combination of a swellable, high molecular weight, water-soluble polymer and a hydroattractant.

Materials useful for sorbing the liquid, active agent formulations are porous particulates that are characterized by high compressibility or tensile strength to withstand compacting forces applied during compacting steps and minimize exudation of liquid, active agent formulation from the pores; low friability so as to preclude or minimize exudation of the liquid, active agent formulation from the particles during compacting steps; and high porosity so as to absorb an adequate of amount of a liquid, active agent formulation to provide an effective amount of active agent in a dosage form. The particles should be adapted to absorb an amount of liquid, active agent formulation such that a therapeutically effective amount of the active agent may be delivered in a unitary dosage form that is of a size that can be conveniently swallowed by a subject and, preferably provided in four or fewer tablets or capsules for ingestion at the same time. The porosity of the particles should be such that at least 5% and up to 70%, more often 20–70%, preferably 30–60%, and more preferably 40–60%, by weight of the liquid, active agent formulation, based on the weight of the particle, may be sorbed into the pores of the particles, while the particles exhibit sufficient strength at such degree of active agent loading so as not to significantly be crushed or pulverized by compacting forces to which the particles may be subjected during manufacturing operations. More typically, the liquid, active agent formulation may comprise 30–40% of the particle weight when the porous particles are crystalline, such as calcium hydrogen phosphate, but that percentage may be greater, for example up to 60–70% when more amorphous materials, such as magnesium aluminometasilicates, are used. Blends of crystalline and amorphous material may be utilized, and at high loadings, it may be advantageous to use blends of calcium hydrogen phosphate particles and amorphous magnesium aluminometasilicate powders. Generally, the polymer/porous particle/liquid, active agent formulation matrix will contain at least 10% of the polymer component to form a gel when in the environment of use.

Preferred materials are those having a strength to resist compression forces of greater than 1500 kg/cm$^2$ without substantial exudation of the liquid, active agent formulation, and most preferably without the tablet hardness plateauing.

A particularly suitable porous particle is exemplified by the particular form of calcium hydrogen phosphate described in U.S. Pat. No. 5,486,365, which is incorporated herein by reference. As described therein, calcium hydrogen phosphate is prepared by a process yielding a scale-like calcium hydrogen phosphate that can be represented by the formula CaHPO$_4$.mH$_2$O wherein m satisfies the expression $0 \leq m \leq 0.5$. Useful calcium hydrogen phosphate materials may include those of the formula CaHPO$_4$.mH$_2$O wherein m satisfies the expression $0 \leq m \leq 2.0$. The scale-like calcium hydrogen phosphate produced has characteristic physical properties that make it particularly suitable for use in the present invention. The scale-like material provides high specific surface area, high specific volume, high capacity for water and oil absorption, and the ability to readily form into spheres upon spray drying. The spherical particulates have excellent flow properties and permit direct compaction into tablets without binders and without significant crushing or pulverizing of the particles during the compaction step.

The scale-like calcium hydrogen phosphate particles generally have a BET specific surface area of at least 20 m²/g, typically 20 m²/g–60 m²/g, a specific volume of at least 1.5 ml/g, typically 2–5 ml/g or more, and an oil and water absorption capacity of at least 0.7 ml/g, typically 0.8–1.5 ml/g. When formed into spheres the spherical particulates may have a mean particle size of at least 50 microns, usually about 70–130 microns. The particle size distribution may be 100% through 40 mesh, 50%–100% through 100 mesh, and 20%–60% through 200 mesh. The bulk density may be from about 0.4 g/ml-0.6 g/ml.

A most preferred form of calcium hydrogen phosphate is that sold under the trademark FujiCalin® by Fuji Chemical Industries (U.S.A.) Inc., Robbinsville, N.J., in types SG and S. Typical parameters for that material include a mean pore size on the order of 70 Angstroms, a mean particle size of about 50–150 microns, a specific volume of about 2 ml/g, a BET specific surface area of about 30–40 m²/g, and an oil and water absorption capacity of about 0.7 ml/g. Type SG typically will have a mean particle size of about 113 microns and a particle size distribution of 100% through 40 mesh, 60% through 100 mesh and 20% through 200 mesh. Type S typically will have a mean particle size of about 68 microns and a particle size distribution of 100% through 40 mesh, 90% through 100 mesh and 60% through 200 mesh. Mixtures of the two types may be conveniently employed to provide particulates having physical characteristics that are suitable for various applications, as may be determined by those skilled in the art of pharmaceutical formulation, tableting and manufacturing.

The calcium hydrogen phosphate has low friability, demonstrating a tensile strength of up to about 130 Kg/cm² when subjected to compressive forces of up to 3000 Kg/cm². The hardness of the tableted material tends not to plateau at compression forces to that limit, while materials such as microcrystalline cellulose (Avicel PH 301), lactose, DI-TAB and Kyowa GS tend to plateau at or about 700–1500 Kg/cm². The angle of repose for the preferred materials typically is on the order of 32–35 degrees.

Another material that may be utilized is that formed of magnesium aluminometasilicate which may be represented by the general formula

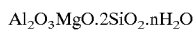
$Al_2O_3MgO.2SiO_2.nH_2O$ wherein n satisfies the relationship $0 \leq n \leq 10$. Commercial magnesium aluminometasilicates are sold as Grades $S_1$, $SG_1$, $UFL_2$, $US_2$, $FH_1$, $FH_2$, $FL_1$, $FL_2$, $S_2$, $SG_2$, $NFL_2N$, and $NS_2N$, under the trademark Neusilin™ by Fuji Chemical Industries (U.S.A.) Inc., Robbinsville, N.J. Especially preferred grades are $S_1$, $SG_1$, $US_2$ and $UFL_2$. Those materials which are amorphous typically have a specific surface area of about 100–300 m²/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g.

Other absorptive materials may be substituted for the foregoing. For example, powders of microcrystalline cellulose sold under the tradenames Avicel (FMC Corporation) and Elcema (Degussa), porous sodiium carboxymethyl cellulose crosslinked, sold as Ac-Di-Sol (FMC Corporation), porous soy bean hull fiber sold under the tradename Fl-1 Soy Fiber (Fibred Group), and porous agglomerated silicon dioxide, sold under the tradenames Cab O Sil (Cabot) and Aerosil (Degussa), may be used.

The liquid, active agent formulation may be in any form that can be dispensed from the inside of the pores as the drug layer disintegrates in the environment of use. The formulation, for example, may be neat, liquid active agent, liquid active agent in a solution, suspension, emulsion or self-emulsifying composition, or the like, or a liposomal solution or solid formulation, or solid active agent in solution, suspension or slurry. Optionally other dosage-forming ingredients, such as an anti-oxidant, a suspending agent, a surface active agent, and the like may be present in the liquid, active agent formulation. The liquid, active agent formulation will be released in a form most suitable to provide active agent to the site of delivery in a state in which it may be rapidly absorbed in the environment of use to provide its beneficial action with minimum delay once delivered to the absorption site.

The present invention has particular utility in the delivery of liquid, active agent formulations that are in the form of emulsions or self-emulsifying compositions. The term emulsion as used in this specification denotes a two-phase system in which one phase is finely dispersed in the other phase. The term emulsifier, as used by this invention, denotes an agent that can reduce and/or eliminate the surface and the interfacial tension in a two-phase system. The emulsifier agent, as used herein, denotes an agent possessing both hydrophilic and lipophilic groups in the emulsifier agent. The term microemulsion, as used herein, denotes a multicomponent system that exhibits a homogenous single phase in which quantities of a drug can be solubilized. Typically, a microemulsion can be recognized and distinguished from ordinary emulsions in that the microemulsion is more stable and usually substantially transparent. The term solution, as used herein, indicates a chemically and physically homogenous mixture of two or more substances.

The emulsion formulations of active agent generally comprise 0.5 wt % to 99 wt % of a surfactant. The surfactant functions to prevent aggregation, reduce interfacial tension between constituents, enhance the free-flow of constituents, and lessen the incidence of constituent retention in the dosage form. The therapeutic emulsion formulations useful in this invention may comprise a surfactant that imparts emulsification comprising a member selected from the group consisting of polyoxyethylenated castor oil comprising 9 moles of ethylene oxide, polyoxyethylenated castor oil comprising 15 moles of ethylene oxide, polyoxyethylene castor oil comprising 20 moles of ethylene oxide, polyoxyethylenated castor oil comprising 25 moles of ethylene oxide, polyoxyethylenated castor oil comprising 40 moles of ethylene oxide, polyoxylenated castor oil comprising 52 moles of ethylene oxide, polyoxyethylenated sorbitan monopalmitate comprising 20 moles of ethylene oxide, polyoxyethylenated sorbitan monolaurate comprising 20 moles of ethylene oxide, polyoxyethylenated sorbitan monooleate comprising 20 moles of ethylene oxide, polyoxyethylenated sorbitan monostearate comprising 20 moles of ethylene oxide, polyoxyethylenated sorbitan monostearate comprising 4 moles of ethylene oxide, polyoxyethylenated sorbitan tristearate comprising 20 moles of ethylene oxide, polyoxyethylenated sorbitan monostearate comprising 20 moles of ethylene oxide, polyoxyethylenated sorbitan trioleate comprising 20 moles of ethylene oxide, polyoxyethylenated stearic acid comprising 8 moles of ethylene oxide, polyoxyethylene lauryl ether, polyoxyethylenated stearic acid comprising 40 moles of ethylene oxide, polyoxyethylenated stearic acid comprising 50 moles of ethylene oxide, polyoxyethylenated stearyl alcohol comprising 2 moles of ethylene oxide, and polyoxyethylenated oleyl alcohol comprising 2 moles of ethylene oxide. The surfactants are available from Atlas Chemical Industries, Wilmington, Del.; Drew Chemical Corp., Boonton, N.J.; and GAF Corp., New York, N.Y.

Typically, an active agent emulsified formulation useful in the invention initially comprises an oil phase. The oil phase of the emulsion comprises any pharmaceutically acceptable oil which is not miscible with water. The oil can be an edible liquid such as a non-polar ester of an unsaturated fatty acid, derivatives of such esters, or mixtures of such esters can be utilized for this purpose. The oil can be vegetable, mineral, animal or marine in origin. Examples of non-toxic oils comprise a member selected from the group consisting of peanut oil, cottonseed oil, sesame oil, olive oil, corn oil, almond oil, mineral oil, castor oil, coconut oil, palm oil, cocoa butter, safflower, a mixture of mono- and di-glycerides of 16 to 18 carbon atoms, unsaturated fatty acids, fractionated triglycerides derived from coconut oil, fractionated liquid triglycerides derived from short chain 10 to 15 carbon atoms fatty acids, acetylated monoglycerides, acetylated diglycerides, acetylated triglycerides, olein known also as glyceral trioleate, palmitin known as glyceryl tripalmitate, stearin known also as glyceryl tristearate, lauric acid hexylester, oleic acid oleylester, glycolyzed ethoxylated glycerides of natural oils, branched fatty acids with 13 molecules of ethyleneoxide, and oleic acid decylester. The concentration of oil, or oil derivative in the emulsion formulation is 1 wt % to 40 wt %, with the wt % of all constituents in the emulsion preparation equal to 100 wt %. The oils are disclosed in *Pharmaceutical Sciences* by Remington, 17$^{th}$ Ed., pp. 403–405, (1985) published by Mack Publishing Co., in *Encyclopedia of Chemistry*, by Van Nostrand Reinhold, 4$^{th}$ Ed., pp. 644–645, (1986) published by Van Nostrand Reinhold Co.; and in U.S. Pat. No. 4,259,323 issued to Ranucci.

The method of this invention may be applied generally to liquid formulations such as those prepared by methods described herein and those contained in commercially-available dosage forms. Examples of commercially available encapsulated liquid formulations that may be utilized include, inter alia, Placidyl® brand of etchchlorvynol, Adalat® brand of nifedipine, VePesid® brand of etoposide, Lanoxicaps® brand of digoxin, Zantac® brand of ranitidine hydrochloride, Sandimmune® and Neoral® brands of cyclosporin, Calderol® brand of calcifediol, Zarontin® brand of ethosuximide, Procardia® brand of nifedipine, Rocaltrol® brand of calcitriol and Vescenoid® brand of tretinoin.

The dosage form may contain an antioxidant to slow or effectively stop the rate of any autoxidizable material present in the dosage form. Representative antioxidants comprise a member selected from the group of ascorbic acid; alpha tocopherol; ascorbyl palmitate; ascorbates; isoascorbates; butylated hydroxyanisole; butylated hydroxytoluene; nordihydroguiaretic acid; esters of garlic acid comprising at least 3 carbon atoms comprising a member selected from the group consisting of propyl gallate, octyl gallate, decyl gallate, decyl gallate; 6-ethoxy-2,2,4-trimethyl-1,2-dihydro-guinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol: polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like. The amount of antioxidant used for the present purposes is about 0.001% to 25% of the total weight of the composition present in the dosage form. Antioxidants are known to the prior art in U.S. Pat. Nos. 2,707,154; 3,573,936; 3,637,772; 4,038,434; 4,186,465 and 4,559,237.

The dosage form may also contain a chelating agent to protect the active agent either during storage or when in use. Examples of chelating agents include, for example, polyacrylic acid, citric acid, edetic acid, disodium edetic acid, and the like. The chelating agent may be co-delivered with the active agent in the environment of use to preserve and protect the active agent in situ. Protection is provided for active agents which are inactivated by chelation with multivalent metal cations such as calcium, magnesium or aluminum that may be present in some foods and are at natural background levels in the fluids of the gastrointestinal tract. Such chelating agents may be combined with the liquid, active agent formulation in the porous particles, or the chelating agents may be incorporated into the matrix in which the porous particles are dispersed.

The liquid formulation may also comprise a surfactant or a mixture of surfactants where the surfactant is selected from the group consisting of nonionic, anionic and cationic surfactants. Exemplary nontoxic, nonionic surfactants suitable for forming a composition comprise alkylated aryl polyether alcohols known as Triton®; polyethylene glycol tertdodecyl throether available as Nonic®; fatty and amide condensate or Alrosol®; aromatic polyglycol ether condensate or Neutronyx®; fatty acid alkanolamine or Ninol® sorbitan mono-laurate or Span®; polyoxyethylene sorbitan esters or Tweens®; sorbitan monolaurate polyoxyethylene or Tween 20®; sorbitan mono-oleate polyoxyethylene or Tween 80®; polyoxypropylene-polyoxyethylene or Pluronic®; polyglycolyzed glycerides such as Labraosol, polyoxyethylated castor oil such as Cremophor and polyoxypropylene-polyoxyethylene-8500 or Pluronic®. By way of example, anionic surfactants comprise sulfonic acids and the salts of sulfonated esters such as sodium lauryl sulfate, sodium sulfoethyl oleate, dioctyl sodium sulfosuccinate, cetyl sulfate sodium, myristyl sulfate sodium; sulated esters; sulfated amides; sulfated alcohols; sulfated ethers; sulfated carboxylic acids; sulfonated aromatic hydrocarbons; sulfonated ethers; and the like. The cationic surface active agents comprise cetyl pyridinium chloride; cetyl trimethyl ammonium bromide; diethylmethyl cetyl ammonium chloride; benzalkonium chloride; benzethonium chloride; primary alkylamonium salts; secondary alkylamonium salts; tertiary alkylamonium salts; quaternary alkylamonium salts; acylated polyamines; salts of heterocyclic amines; palmitoyl carnitine chloride, behentriamonium methosulfate, and the like. Generally, from 0.01 part to 1000 parts by weight of surfactant, per 100 parts of active agent is admixed with the active agent to provide the active agent formulation. Surfactants are known to the prior art in U.S. Pat. Nos. 2,805,977; and in 4,182,330.

The liquid formulation may comprise permeation enhancers that facilitate absorption of the active agent in the environment of use. Such enhancers may, for example, open the so-called "tight junctions" in the gastrointestinal tract or modify the effect of cellular components, such a p-glycoprotein and the like. Suitable enhancers include alkali metal salts of salicyclic acid, such as sodium salicylate, caprylic or capric acid, such as sodium caprylate or sodium caprate, and the like. Enhancers may include the bile salts, such as sodium deoxycholate. Various p-glycoprotein modulators are described in U.S. Pat. Nos. 5,112,817 and 5,643,909, which are incorporated herein by reference. Various other absorption enhancing compounds and materials are described in U.S. Pat. No. 5,824,638, which also is incorporated herein by reference. Enhancers may be used either alone or as mixtures in combination with other enhancers.

Representative examples of the swellable polymer comprising high molecular weight, water-soluble polymers are polyethylene oxide and cellulosic polymer derivatives including hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyls, polyvinyl alcohol, polyacrylic acids, alginates, gelatin, natural gums, including guar, lightly crosslinked versions of these polymers,starches, starch graft copolymers and the like. The polymers generally have number average molecular weights over 50,000 grams per mole, such as between 50,000 and 10,000,000 grams per mole and representative viscosities, e.g. for polyethylene oxide in the range of 12–20,000 cps (5% aq, 250° C., MW 100,000–900,000), 400–4000 cps (2% aq, 25° C., MW 1,000,000–2,000,000) and 1500–15,000 cps (1% aq, 25° C., MW 4,000,000–8,000,000) [Brookfield viscometer, rotational spindle]; for methylcellulose in the range of 1,500–18,000 cps (2% aq, 20° C., MW62,000–134,000) [Ubbelohde tube viscometer]; for hydroxypropyl methylcellulose in the range of 4,000–100,000 cps (2% aq, 20° C., MW 88,000–242,000) [Ubbelohde tube viscometer]; for hydroxyethyl cellulose in the range of 75–400 cps (5% aq, 25° C., MW 90,000–200,000), 400–6500 cps (2% aq, 25° C., MW 300,000–720,000) and 1500–5,000 cps (1% aq, 25° C., MW 1,000,000–1,300,000) [Brookfield viscometer, rotational spindle]; for guar about 5100 cps (1%) [Brookfield viscometer, rotational spindle]; for poly(methyl vinyl ether/maleic anhydride) in the range of 15 to greater than 200 cps (5% aq., MW 20,000–80,000) [Brookfield viscometer, rotational spindle]; for polyvinyl alcohol in the range 27–65 cps (4% aq, 20° C. [Hoeppler falling ball method and 1100–1500 cps (10%aq, 25° C.) [Brookfield viscometer, rotational spindle; for sodium carboxymethyl cellulose in the range of 25–50 cps (2% aq, 25° C.) (MW 90,000) to about 2,500–6,000 cps (1% aq, 25° C.) (MW 700,000) [Brookfield viscometer, rotational spindle]; and for sodium polyacrylic acid 5000–80,000 (0.5% aq) (MW 750,000–4,000,000) [Brookfield viscometer, rotational spindle]. Polymers having molecular weights between 300,000 and 8,000 000 grams per mole are preferred, and those having molecular weights between about 2,000,000 to 8,000,000 grams per mole are especially preferred. Polyethylene oxide having a number average molecular weight between about 5,000,000 to 8,000,000 grams per mole is most especially preferred, e.g. Polyox 303 and Polyox 308. Also, especially preferred are methylcellulose type/grade A15C, A4M, A18M and hydroxypropyl methylcellulose type/grade K4M, K15M, K100M, E4M and F4M (Dow Chemical Company); hydroxyethyl cellulose such as Natrosol® HEC; hydroxypropyl cellulose such as Klucel (Grades H, M, G, J, L, E—Aqualon Company); guar such as Supercol® Guar U (Aqualon Company); pectin such as GENU Pectin (Aqualon Company); carrageenan such as GENU Carrageenan (Aqualon Company); poly(methyl vinyl ether/maleic anhydride) such as Gantrez® AN Copolymer (AN-119, -139, -149, -169, -179, GAF Corporation); polyvinyl alcohol such as Elvanol® 71–30, Elvanol® 85–80, Elvanol® 55–65, Elvanol® 50–42 and Elvanol® HV (DuPont); sodium carboxymethyl cellulose such as Aqualon cellulose gum grade 7H4; polyacrylic acids such as Carpobol® resin grades 971 P, 974P, 980, 981, 1382, 2984, 5984, ETD 2001, ETD 2050, calcium polyacrylic acids such as Noveon® resin grades M-1, CA-1 and CY-2, and sodium polyacrylic acid (BF Goodrich, Cleveland, Ohio).

Representative examples of hydroattractants are water-insoluble polymers such as low substituted hydroxypropyl cellulose, microcrystalline cellulose (Avicel), cross-linked sodium or calcium carboxymethyl cellulose, cellulose fiber (Solka-Floc or Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, wheat starch granules, sodium carboxymethyl starch (Expotab, Primojel), corn starch/acrylamide/sodium acrylate copolymer, acrylamide/sodium acrylate copolymer and the like. A particularly suitable hydroattractant is hydroxypropyl cellulose having a hydroxypropyl content of between about 8–15 weight percent, and preferably about 10–13 weight percent, such as that supplied as Low Substituted Hydroxypropyl Cellulose grade 11 as manufactured by Shin-Etsu Chemical Company, Ltd., Tokyo, Japan. Optionally, non-polymeric water-soluble hydroattractants can be incorporated. These include sodium chloride, sugars such as sorbitol, mannitol, glucose, maltose, sucrose, lactose, acids such as citric acid, tartaric acid, succinic acid, gas-generating agents such as sodium or potassium bicarbonate which react with gastric fluids to produce carbon dioxide gas, and the like.

Typically, the water soluble, high molecular weight polymer in the polymer matrix is present in from about 5% to about 90% by weight based on the total weight of the active agent formulation matrix, and the hydroattractant is present in from about 5% to about 70% by weight based on the total weight of the active agent formulation matrix. The particular percentages may be chosen to provide the desired retention time in the stomach and the desired release profile of active agent. However, it is presently preferred to have the polymer matrix contain from about 10 weight percent to about 50 weight percent of the water soluble, high molecular weight polymer and from about 10 weight percent to about 60 weight percent of the hydroattractant, with weight percentages of water soluble, high molecular weight polymer in the range of 10 to 40 weight percent and hydroattractant in the range of 25 to 35 being especially preferred.

Dosage form 10 is conveniently cylindrically shaped with rounded ends that facilitate administration of the dosage form in its non-swelled state. In FIG. 1A, the device 10 is shown in preparation prior to application of the insoluble material or band 15 shown in FIG. 1B. The insoluble material exemplified as band 15, circumscribes a portion of the outer surface of the polymer matrix 11. While a single band is illustrated in FIG. 1, additional bands such as illustrated in FIG. 4 can be utilized depending on the particular application for which the device is being used.

The band of insoluble material 15 is applied to the outer surface of the polymer matrix. The insoluble material imparts rigidity to the gel-forming polymer matrix to manage gastric retention time and further control the delivery profile of the active agent of interest. Band 15 typically exhibits low water permeability and will prevent that portion of the polymer matrix which it surrounds from imbibing fluid, thus substantially limiting any swelling of polymer matrix 11 at that location. The number, size, and placement of the insoluble bands that are applied onto the surface of the active agent formulation matrix may be varied to adjust the active agent delivery profile and the retention time in the stomach. For example, bands 0.1 mm to about 12 mm in width, preferably between about 0.5 and 8 mm, may be applied onto the active agent formulation matrix surface. Further, between about 1 and 10 bands may be used, but generally between about 1 and 3 are affixed to the matrix. The bands may be placed close together (i.e., within about 0.5 mm of each other) or may be placed about 8 to 12 mm apart.

Figure 4A:
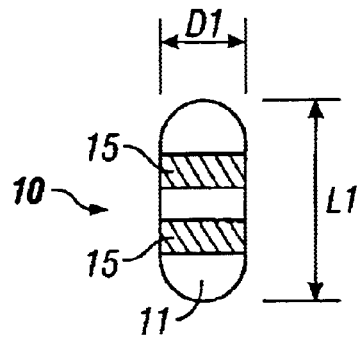
FIGS. 4A–4D illustrate an embodiment of the invention having multiple, insoluble bands on the surface of the dosage form.
Figure 4B:
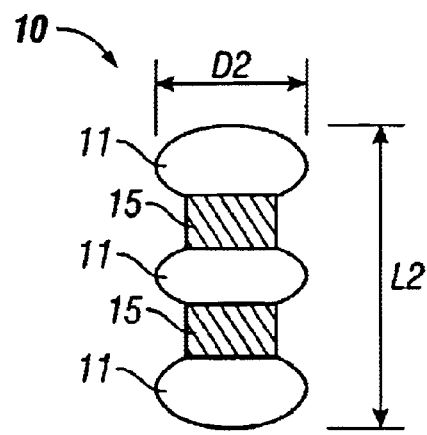
Figure 4C:
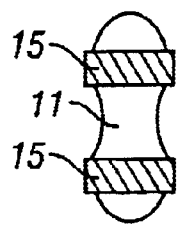
Figure 4D:
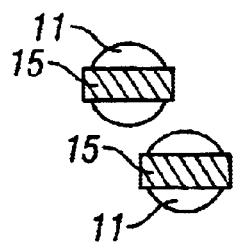

With reference to FIGS. 4A–4D, dosage form 10 is formed with two bands 15, each circumscribing a portion of the surface of polymer matrix 11 in which active agent (not shown) is dispersed. FIG. 4A illustrates dosage form 10 in its initial configuration before it has imbibed any fluid. Upon administration to a subject, dosage form 10 swells as shown in FIG. 4B in those segments of polymer matrix 11 that are not surrounded by bands 15. Because of the low fluid impermeability of bands 15, those portions of polymer matrix 11 surrounded by bands 15 do not appreciably imbibe fluid and the polymer in such segments of the polymer matrix does not swell to any significant extent. FIGS. 4C and 4D illustrate sequential states of dosage form 10 after it is substantially eroded by gastric fluid and contractions of the stomach. Eventually, dosage form 10 will separate into two pieces and be expelled from the stomach.

The insoluble material comprising band(s) 15 may be any material that is nontoxic, biologically inert, nonallergenic and nonirritating to body tissue, that exhibits little impermeability to liquids, and that maintains its physical and chemical integrity in the environment of use for at least a portion of the dispensing period. The bands may be formulated with neutral charge polymers which are insoluble in gastric fluid or may be formulated with anionic polymers which are insoluble in gastric fluid and dissolve in intestinal fluid. The low liquid permeability of the insoluble material serves to limit swelling of the polymer matrix in that section of the polymer matrix that is surrounded by the band.

Insoluble materials from which the bands may be prepared include, for example, polyethylene, polystyrene, ethylene-vinyl acetate copolymers, polycaprolactone and Hytrel® polyester elastomers (Du Pont). Additional banding materials include but are not limited to polysaccharides, cellulosics, cellulose acetate, cellulose acetate propionate, cellulose acetate butyrate, cellulose acetate pseudolatex (such as described in U.S. Pat. Nos. 4,931,285 and 5,024,842), cellulose acetate propionate, cellulose acetate butyrate, ethyl cellulose, ethyl cellulose pseudolatex (such as Surelease® as supplied by Colorcon, West Point, Pa. or Aquacoat™ as supplied by FMC Corporation, Philadelphia, Pa.), nitrocellulose, polylactic acid, poly-glycolic acid, polylactide glycolide copolymers, polycaprolactone, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, methacrylic acid copolymers, copolymers of methylmethacrylate and ethylacrylate, ammoniomethacrylate copolymer, latex of acrylate esters (such as Eudragit® supplied by RöhmPharma, Weiterstadt, Germany), polypropylene, copolymers of propylene oxide and ethylene oxide, propylene oxide ethylene oxide block copolymers, ethylenevinyl alcohol copolymer, polysulfone, ethylene vinylalcohol copolymer, polyxylylenes, polyamides, rubbers, such as styrenebutadiene, polyisobutylene and the like, natural and synthetic waxes, paraffin, carnauba wax, petroleum wax, white or yellow bees wax, castor wax, candelilla wax, rice bran wax, microcrystalline wax, stearyl alcohol, cetyl alcohol, bleached shellac, esterified shellac, chitin, chitosan, silicas, polyalkoxysilanes, polydimethyl siloxane, polyethylene glycol-silicone elastomers, crosslinked gelatin, zein, electromagnetic irradiation crosslinked acrylics, silicones, or polyesters, thermally crosslinked acrylics, silicones, or polyesters, butadiene-styrene rubber, glycerol ester of partially dimerized rosin, glycerol ester of partially hydrogenated wood rosin, glycerol ester of tall oil rosin, glycerol ester of wood rosin, pentaerythritol ester of partially hydrogenated wood rosin, pentaerythritol ester of wood rosin, natural or synthetic terpene resin and blends of the above.

The banding materials often are also formulated with plasticizers, and optionally with wetting agents, surfactants, opacifiers, colorants, flavorants, taste-masking agents, and the like. Examples of typical plasticizers are as follows: polyhydric alcohols, polyethylene glycol, glycerol, propylene glycol, acetate esters, glycerol triacetate, triethyl citrate, acetyl triethyl citrate, tributyl citrate, acetyl tributyl citrate, glycerides, acetylated monoglycerides, oils, mineral oil, castor oil, PEG castor oil, and the like.

Figure 2:
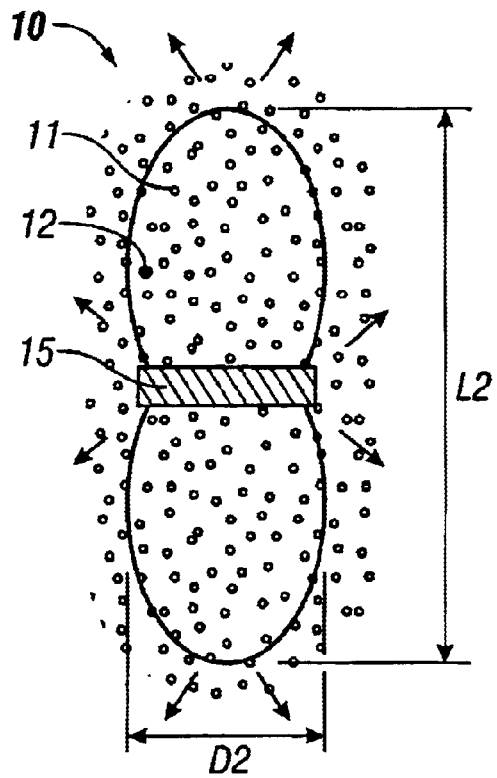
FIG. 2 illustrates the device of FIG. 1B in its initially-swollen state after having expanded in the stomach.

Referring again to the embodiment of the invention depicted in FIG. 1A, the polymer matrix 11 in its non-swelled state has a length L1 and a maximum diameter D1 intermediate the ends. FIG. 2 shows dispensing device 10 after having been placed in the stomach. The active agent formulation matrix 11 on each side of the band 15 has swelled from imbibing fluid from the stomach and begun to erode, thereby releasing porous particles 12 to the stomach environment. In contrast to the exposed segments of the swollen polymer matrix 11, band 15 and the portion of the polymer matrix beneath it have not swelled to such an extent. Accordingly, that segment of the polymer matrix surrounded by band 15 is maintained in a constrained and more compressed, non-swollen state than the unbanded portion of the matrix. Since band 15 does not take up an appreciable amount of fluid from the stomach and swell, band 15 retains its substantially rigid or semi-rigid form, and provides an element of rigidity to the dosage form as a whole. While it is not entirely clear how band 15 and the constrained segment of polymer matrix 11 facilitate retention of the dosage form in the stomach through housekeeping waves, it is thought that the band reduces the rate of erosion of the polymer matrix, thus maintaining a larger effective size of the dosage form and reducing the chance for its expulsion from the stomach, for a longer period of time than would otherwise occur if the band was not present. Additionally, the presence of the band on the polymer matrix provides a semi-rigid segment of the dosage form that appears to cause the dosage form to be retropelled into the main area of the stomach as a reaction to the stomach contractions rather than being expelled by the housekeeping wave, as a less rigid gel would be inclined to be.

After swelling, the dosage form 10 has a length L2 and a maximum diameter D2 measured at the widest part of the swollen polymer matrix. Generally, for human applications the largest dimension of the device in the swollen state equivalent to the diameter D2 should be greater than 7 mm, preferably 10 mm or greater, and most preferably 13 mm or greater during the period of residence in the stomach when active agent is being dispensed. Since the dosage form is intended to remain in the stomach for a prolonged retention period, the effective diameter of the active agent dosage form in when in its swollen state in the stomach may have to be significantly larger than 13 mm, and may extend to more that 50 mm or greater. Larger dosage forms may be appropriate particularly when the polymer matrix is designed to erode relatively rapidly over time in order to provide the required delivery of active agent for therapeutic effect. For applications in animals other than humans, for example in dogs, the maximum diameter should be greater than about 2 mm.

The maximum dimension for any particular dosage form will depend on the particular application and animal in which the device is being used. Such dimensions can be determined by those skilled in the art in accordance with the teaching herein and the various patents and publications noted herein and existing in the related art. A practical consideration, particularly for oral administration to humans, is that the initial size of the device be such that it can be reasonably, comfortably swallowed. For human oral applications, a preferred size of the device in its form prior to administration to the stomach would be on the order of a size 000 capsule to a size 5 capsule. However, it is understood that smaller or larger sizes could be used for particular applications where necessary.

Since the dosage forms of the invention may be gel-forming, it may be desirable to wet the outer surface of the dosage form immediately prior to the subject swallowing the dosage form in order to provide a more slippery outer surface and promote ease of swallowing. Alternatively, the matrix core can be inserted into a hard gelatin capsule prior to application of the band in order to facilitate swallowing and also promote ease of manufacture in applying and forming the bands. Upon entering the stomach, that portion of the hard gelatin capsule that is not covered by the band will dissolve, exposing the polymer matrix to fluid in the stomach. As the polymer matrix imbibes fluid, the dosage form will swell in the exposed segments as previously described. The dosage form typically is prepared to allow for swelling at a controlled rate, particularly at a limited initial rate, so that the dosage form does not swell inordinately during the swallowing process and result in obstruction of the esophagus.

It is preferred that the dosage forms of this invention be administered when the subject is in the fed state to allow time for maximum swelling of the polymer matrix prior to the housekeeping wave being initiated. Generally a meal size that results in a delay of the housekeeping wave of from about 1 to 3 hours is satisfactory. It may be preferable to administer one or more of the dosage forms at the start of each dosing period, depending on the size of the dosage form, to facilitate swallowing and yet provide sufficient dose of active agent. Particularly in those instances where the dosage form is near the lower end of the size range, i.e., the maximum diameter along the longitudinal axis is on the order of 7–13 mm, it is preferable that the dosage form be administered to the subject in the fed state to allow for significant swelling of the dosage form prior to the housekeeping wave occurring. Typically, administration will occur with the meal or within two hours thereafter, and preferably within one hour of completion of the meal. Depending on the half-life of an active agent, once-a-day dosing could conveniently occur with or after dinner. For b.i.d. (i.e., twice-a-day) dosing to a human subject, the dosage form can conveniently be administered with or after breakfast and dinner, but, if after, preferably within one or two hours after conclusion of the meal. For more frequent administration, such as t.i.d., the dosage form may be administered after breakfast, lunch and dinner. For administration within usual meal patterns, it is desirable that the subject consume small amounts of food or liquids prior to administration of the dosage form. The dosage form may be administered prior to the taking of food if administered with a sufficient quantity of liquid so as to delay onset of the housekeeping wave, until consumption of food is initiated.

To facilitate retention of the dosage forms of the invention, particularly if the dosage form is to be administered to a subject in the fasted state, it may be desirable to combine one or more gastric-emptying delaying agents with the active agent composition or coat the dosage form with a composition containing a gastric-emptying delaying agent, i.e., a substance that delays onset of the housekeeping wave of the IMMC. Examples of agents for delaying onset of the housekeeping wave, preferably locally delivered by the dosage form in amounts not resulting in any substantial systemic effect to the subject, as for example, anticholenergic agents such as propantheline, and other agents including, but not limited to, methylcellulose, guar gum, fats such as triglyceride esters, e.g., triethanol myristate, fatty acids of 10–15 carbon atoms, and the like.

Figure 3A:
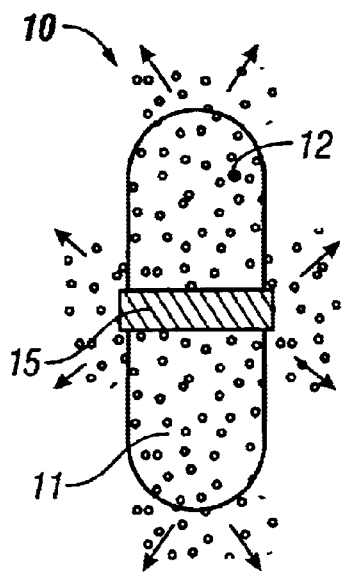
FIGS. 3A and 3B illustrate the device of FIG. 2 at later stages where the device has eroded in the fluid environment of use.
Figure 3B:
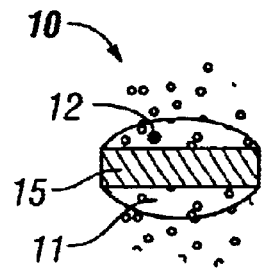

FIGS. 3A and 3B show dosage form 10 after a length of time in the fluid environment of the stomach. Polymer matrix 11 has eroded at the exposed surface of the matrix, i.e., those portions of the matrix not covered by the insoluble material 15 to such an extent that the device 10 is smaller than its initial swollen configuration. Erosion of the matrix permits release of the porous particles from the matrix. After the porous particles are released, the liquid, active agent may elute by diffusion or convection from the pores into the environment of use. Additionally, as the released porous particles disintegrate in the gastric environment, the liquid, active agent formulation will be directly released into the environment of use. At some point, the matrix may erode to such an extent that the remainder of the dosage form is expelled from the stomach. Band 15 will be expelled from the stomach either alone, if it has separated from the dosage form at some time near the end of the delivery period, or as part of the remainder of the dosage form expelled from the stomach. In some applications, it may be desirable to form band 15 with weakened portions so that band 15 splits and falls away from the polymer matrix after some predetermined time in the stomach to permit a particular release pattern of active agent from the dosage form over the delivery period.

The liquid, active agent formulation of the dosage form may optionally be formulated with inorganic or organic acids or salts of drugs which promote dissolution and disintegration or swelling of the porous particles upon contact with biological fluids. The acids serve to lower the pH of the microenvironment at the porous particle, and promote rapid dissolution of a particle, such as calcium hydrogen phosphate, that is soluble in low pH environments, thus providing rapid liberation of the liquid, active agent formulation contained in the porous particle. Examples of organic acids include citric acid, tartaric acid, succinic acid, malic acid, fumaric acid and the like. Salts of drugs where the anion of the salt is acidic, such as acetate, hydrochloride, hydrobromide, sulfate, succinate, citrate, and the like, can be utilized to produce immediate disintegration and dissolution of the porous particle. A more complete list of acidic components for this application is provided in Journal of Pharmaceutical Sciences, "Pharmaceutical Salts", Review Articles, January, (1977), Vol. 66, No. 1, pages 1–19. The interaction of an acidic component with a porous particle of, for example, calcium hydrogen phosphate, in the presence of water from gastric fluids accelerates dissolution of the particle at a greater rate than gastric fluid alone, producing a more rapid and complete release of the liquid, active agent formulation into the environment of use. Likewise alkaline components or salts of drugs where the cation of the salt is alkaline such as choline may be incorporated into the liquid, active agent formulation to promote rapid and complete dissolution of a porous particle which is soluble or swells at elevated pH. Such a particle may be formed, for example, of poly(methacrylic acid-methyl methacrylate) 1:2 available commercially as Eudragit S100 (Rohm America, Sommerset, N.J.

The dosages forms of in this invention can be prepared by standard methods from the materials previously described.

Typically, the liquid, active agent formulation will be prepared independently of the porous particle; although in some circumstances, it may be desirable to combine the formation of the liquid, active agent formulation with the mixing of the formulation components and the porous particles. As described previously, the liquid formulation may be a solution, suspension, dispersion, emulsion, etc. depending on the particular application for which the dosage form is intended.

After, the liquid, formulation is prepared, the desired quantity of liquid, active agent formulation and porous particles may be mixed in a blender to sorb the liquid into the porous particles. That mixture may be milled by passing it through mesh screens to insure intimate mixing and complete absorption of the liquid, active agent formulation into the porous particles. The wet granulation may then be dried at ambient conditions to facilitate handling. However, the drying conditions are not so severe as to evaporate a significant amount of the liquid of the liquid, active formulation. Also, to facilitate handling, it may be desirable to add a small amount of another absorbent, such as a soluble sugar, e.g., maltose or the like, that will readily dissolve in the environment of use when the porous particle is released from the dosage form, but not subsequently change the desired release characteristics of the dosage form. Small amounts of inert absorbents, such as mircocrystalline cellulose or silicon dioxide, may be substituted for the soluble material, but, again, the quantities should not be so great that the desired release characteristics of the liquid, active agent formulation from the absorbent particles is significantly affected. Another method of manufacture would be to sorb the liquid, active agent formulation into the particles in a fluidized bed of the particles. Those and other methods are conventional and will be apparent to those skilled in the art.

An appropriate quantity of porous particles, containing the liquid, active agent formulation, and the polymer ingredients are separately passed through a screen, such as a screen having a mesh of about 40 wires per inch, to reduce any larger sized materials, and dry mixed. Then, a pharmaceutically-acceptable liquid, having a sufficient vapor pressure to allow subsequent drying over a reasonable period of time, for example 24 hours, is added to the dry mixture and the damp mass is extruded through a mesh screen (e.g. 20 wires per inch) to further mix the materials. Examples of suitable liquids are water, methanol, ethanol, isopropanol, acetone, ethyl acetate and the like. The liquid will need to be compatible with the liquid of the liquid, formulation.

After the extrusion process, the mixture is allowed to dry, for example in air overnight at room temperature, if the active agent does not require any special handling. After drying, the resulting material is granulated, for example by passing the dried material through a mesh screen (e.g., 20 wires per inch). The granules are combined with a suitable tableting lubricant which has been previously passed through a mesh screen (e.g., 60 wires per inch). The resulting material is tumbled to produce the finished granulation for the tableting process. Tablets are produced using well known methodologies associated with horizontal and vertical compression units using dies and punches of appropriate dimensions. Alternate granulation methods, for example, fluid bed granulation or direct compression granulation can be used as well and such method will be chosen by one skilled in the art depending on the particular nature of the materials being used and the convenience and preference of the fabricator.

In order to prepare a preferred device of the present invention, the active agent formulation is first prepared and formed into a matrix of the desired size and shape. The matrix in its initial prepared form is about the size and dimensions of a size "000" to size 5 hard gelatin capsule. The cross-sectional shape of the matrix may be generally circular or may be oval, triangular, square, hexagonal or other shapes that are easily handled, especially by patients with limited dexterity. Presently preferred shapes are those in which the cross-section is circular or oval. The ring or bands are then placed onto the surface of active agent formulation matrix or printed onto the surface using conventional banding or printing techniques, such as disclosed herein or in U.S. Pat. No. 5,534,263, which is incorporated herein by reference.

The terms "active agent" and "drug" are used interchangeably herein and refer to an agent, active agent, compound, composition of matter or mixture thereof which provides some pharmacologic, often beneficial, effect. This includes foods, food supplements, nutrients, drugs, antiacids, vitamins such as, for example, Vitamin C, Vitamin E, microorganism attenuators and other agents that benefit the environment of use. As used herein, the terms include any physiologically or pharmacologically active substance that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. The active agent that can be delivered includes inorganic and organic compounds, including, without limitation, active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system.

Suitable active agents may be selected from, for example, proteins, enzymes, enzyme inhibitors, hormones, polynucleotides, nucleoproteins, polysaccharides, glycoproteins, lipoproteins, peptides, polypeptides, steroids, hypnotics and sedatives, psychic energizers, tranquilizers, anticonvulsants, antidepressants, muscle relaxants, antiparkinson agents, analgesics, immunosuppressants, antiinflammatories, antihistamines, local anesthetics, muscle contractants, antimicrobials, antimalarials, antivirals, antibiotics, antiobesity agents, antidiabetic agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antidiabetics, immunosuppressives, antidepressants, antiobesity agents, antihyperglycemics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, acrivastine, benazepril, carbamazipine, chlorothiazide, desmopressin, dicumarol, furosemide, gepirone griseofulvin, levodopa/benserazide, llithium, methylphenidate, 8-methoxalen, metoprolol, misoprostol, octreotide, phenobarbital, phenytoin, piretanide, paraastatin, propoxyphen, riboflavin, sertaline, spironolactone, sumatriptan, ticlopidine, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, carbidopa, carbidopa/levodopa, selegiline, chlorpromazine, methyldopa, dihydroxyphenylalanine, calcium gluconate, ketoprofen, ibuprofen, colchicine, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The present invention is particularly useful to deliver active agents that are poorly absorbed in the lower gastrointestinal tract, but well absorbed in the upper gastrointestinal tract (i.e., the small intestine) or active agents that exhibit poor solubility such that the increased retention time in the stomach allows for a greater quantity of active agent to dissolve from the dosage form than would otherwise be dissolved. Typically, antiviral, antifungal and antibiotic agents, e.g. sulfonamides, quinolones, penicillins, cephalosporins, aminoglycosides, and tetracyclines, are representative classes of agents for which the invention is particularly useful. Such antibiotic agents may include, for example, β-lactam antibiotics, vancomycin, clidamycin, erthromycin, clarithromycin, 14-hydroxy clarithromycin, azithromycin, roxithromycin, dirithromycin, trimethoprim-sulfamethoxaazole, rifampin, ciprofloxacin, amoxicillin, clindamycin, ceftriaxone, cefotaxime, chloramphenicol, clindamycin, cefoxitin, doxyclycline, spectinomycin, ofloxacin, rifampin, minocycline, doxycycline, aztreonam, imipenem, meropenem, nitrofurantoin, azithromycin, atovaquone, trimetrexate, dapsone, primaquin, trimetrexate, ketoconazole, floconazole, amphotericin B, itraconazole, trifluridine, foscarnet, zidovudine amantadine, interferon alfa, sulfonamides such as sulfisoxazole, sulfadiazine, and sulfasalazine, quinolones and fluoroquinolones such as, for example, cinoxacin, forfloxacin, diprofloxacin, ofloxacin, spardlosxacin, lomefloxacin, fleroxacin, pefloxacin and amifloxacin, gentamicin, tobramycin, amikacin, netilmicin, kanamycin,and neomycin. Representative antiviral agents include acyclovir, famciclovir, foscarnet, ganciclovir, ritonavir, idoxuridine, sorivudine, trifluridine, valacylcovir, vidarabine, didanosine, stavudine, zalcitabine, zidovudine, amantadine, interferons, e.g., interfon alpha, ribavirin, rimantadine, nucleoside RT inhibitors, such as lamivudine and adeforvir, non-nucleoside inhibitors such as nevrapine, delavairidine, lviride, saquinavir and indinavir, nucleoside DNAp inhibitors such as famciclovir, fialuridine, cidofovir and lobucavir, antisense oligonucleotides such as afovirsen, receptor decoys such as sICAM-1, capsid binding agents such as pirodavir, and neuraminidase inhibitors such as GG167.

Specific examples of active agents that are readily absorbed in the upper gastrointestinal tract relative to the lower gastrointestinal tract are acyclovir, ganciclovir, cimetidine, ranitidine, captopril, methyldopa, selegiline and the like. Specific examples of active agents that exhibit poor solubility in water are diphenidol, meclizine hydrochloride, hydralazine, prochloperazine maleate, phenoxybenzamine, triethylperazine maleate, anisindone, diphenadione erythrityl tetranitrate, digoxin, isofllurophate, acetazolamide, methazolamide, bendroflumethiazide, chlorpropamide, tolazamide, chlormadionone acetate, phenaglycodol, allopurinol, alluminum aspirin, methotrexate, acetyl sulfisoxazole, erythromyciin, progestins, esterogenic, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiool 3-methyl ether, pednisolone, 17-alpha-hydroxyprogesterone acetate, 19-norprogesterone, norgestrel, norethindrone, progesterone, norgesterone, norethlynodrel, and the like.

Retention of the device of the present invention in the stomach for a prolonged period of time make it especially useful for the localized treatment of gastric acidity and gastrointestinal disorders such as duodenal ulcers, peptic ulcers and chronic gastritis, particularly those resulting from the presence of *Helicobacter pylori*. Representative active agents for such uses include cimetidine, rantitidine, famotidine, nizatidine, zolentine, omeprazole, lansoprazole and active agents useful for the treatment of *Helicobacter pylori*, such as metronidazole, timidazole, amoxicillin, clarithromycin, minocycline and tetracycline.

The dosage form of the invention is useful for the delivery of oral, hypoglycermic agents, such as the sulfonylureas, e.g., tolbutamide, glyburide, glipizide and gliclazide, the biguamides, e.g., metformin and phenformin, and the thiazolidinediones, e.g. ciglitazone and pioglitazone. Also, immunosupressives, such as, for example, cyclosporine, tacrolimus (Fk506) and micophenolate mofetil.

While for reasons of efficacy, safety, economy, convenience and/or efficiency it may be desirable to utilize a single active agent in the active agent formulation, it is to be understood that more than one active agent may be incorporated into the active agent formulation in a device of this invention, and that the use of the term "agent" or "active agent" in no way excludes the use of two or more such agents or active agents. The agents can be in various forms, such as uncharged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed. Combinations of two or more active agents can optionally be co-delivered, simultaneously or sequentially from the dosage form of this invention.

The dosage form may include additional ingredients, such as, for example, a buffer or other agents for controlling pH in the stomach or elsewhere in the gastrointestinal tract, an agent or agents for delaying onset of the housekeeping wave, preferably locally delivered by the dosage form in amounts not resulting in any substantial systemic effect to the subject, as for example, anticholenergic agents such as propantheline, and other agents including, but not limited to, methylcellulose, guar gum, fats such as triglyceride esters, e.g., triethanol myristate, fatty acids of 10–15 carbon atoms, and the like, a viscosity regulating vehicle, a surfactant, a dye, a permeation enhancer, a proteinase inhibitor, or other formulation ingredients and additives, as are known in the art.

The dosage form may also include minor amounts of low molecular weight polymers which serve useful functions in tablet formation, for example, to improve the tablet cohesiveness after compression or to improve the physical or chemical stability of the dosage form. These polymers are added at quantities less than 10% by weight and preferably less that 5% by weight of the tablet. Examples of such polymers include hydroxypropyl methyl cellulose having molecular weights of less that 20,000 grams per mole, methycellulose having a molecular weight of less than 20,000 grams per mole, polyvinyl pyrrolidone having a molecular weight of less than 360,000 grams per mole, and the like.

The amount of active agent employed in the dosage form will be that amount necessary to deliver a therapeutically effective amount of the agent to achieve the desired therapeutic result. In practice, this will vary widely depending upon the particular agent, the degree of active agent absorption, the severity of the condition, and the desired therapeutic effect. Thus, it is not practical to define a particular range for the therapeutically effective amount of each active agent incorporated into the device. Such ranges can easily be determined by one skilled in the art using conventional methods, for example from dose ranging and plasma level studies. Any references to specific quantities of active agent or specific dose ranges of active agent herein are intended to include the amount or amounts of active agent specified and bioequivalents thereof.

When the delivery device of this invention is being used to substitute for one or more doses of an active agent presented in a conventional dosage form that is usually prescribed for multiple dosing during a predetermined period, the sum of the amounts of active agent present in the multiple doses of the conventional dosage form for use in the period may be used to determine an upper limit on the of the amount of active agent to be included in the device of this invention. For example, if the conventional dosage form contains 200 mg of active agent and is to be administered every 3 hours, a dosage form of this invention may be prepared for administration every 6 hours, and that dosage form may contain 400 mg of active agent which will be delivered over the 6 hour period.

However, when compliance with multiple dosing is a problem, the advantage of administering the dosage forms of the invention at fewer times throughout a twenty-four hour period may provide incentive to incorporate greater amounts of active agent, where such greater amounts do not have any deleterious effects. The specific amount of active agent to be included in the dosage form of the invention can easily be determined by routine dosage studies that compare the blood plasma active agent levels of subjects with conventional dosing and the dosage form of this invention.

The dosage forms of this invention can conveniently release active agent in a controlled and sustained manner over a prolonged period. Typically, active agent will be released from the dosage form at a rate that releases a therapeutically effective amount of active agent to the subject over a substantial portion of the period between administration of the dosage forms. Typically, release will occur over 40% of the period between repeated administration of the dosage form, more preferably at least over 60% of the period, and most preferably over 80% of the period.

In an especially preferred embodiment, the invention comprises porous particles in which is sorbed liquid, active agent formulation dispersed in a polymer composition having from about 10 weight percent to about 50 weight percent of a water-soluble, high molecular weight polyethylene oxide polymer and from about 10 weight percent to about 60 weight percent of a water-insoluble hydroxypropyl cellulose polymer. The polyethylene oxide polymer has a molecular weight of between about 100,000 and 10,000,000 grams per mole. The hydroxypropyl cellulose polymer preferably has a hydroxypropyl content of between about 8–15 weight percent, and most preferably between about 10–13 weight percent.

The following examples are illustrative of the present invention. They are not to be construed as limiting the scope of the invention. Variations and equivalents of these examples will be apparent to those skilled in the art in light of the present disclosure, the drawings and the claims herein.

Preparation 1

A general procedure for preparing the dosage forms of the present invention is described below with the exemplary active agent being cyclosporin. Various other materials or additives as described herein may be used in place of or in addition to the specific materials provided in this description in the same or other proportions based on the desired final characteristics of the dosage forms to be fabricated.

A self-emulsifying drug solution comprising, in weight percent, 2% cyclosporin, 49% polyoxyl 35 castor oil (Cremophor EL, BASF Corporation) and 49% distilled acetylated monoglyceride (Myvacet 9–45) is prepared. Then, 15 g of the solution is blended with 35 g of porous calcium hydrogen phosphate (FujiCalin) in a mixing vessel. 3.6 Grams of the gel-forming polymer polyethylene oxide, having a number average molecular weight of approximately 7 million grams per mole, is separately screened through a mesh having 40 wires per inch. The polyethylene oxide is supplied under the trade name Polyox® grade 303 as manufactured by Union Carbide Corporation, Danbury, Conn. The sized active agent and polymer are mixed. Then, 8.25 grams of a hydroattractant water-insoluble polymer, hydroxypropyl cellulose having a hydroxypropyl content of 10–13 weight percent and an average fiber particle size of 50 microns, is sieved through the 40-mesh screen and blended into the mixture. The hydroxypropyl cellulose is supplied as Low-Substituted Hydroxypropyl Cellulose grade 11 as manufactured by Shin-Etsu Chemical Company, Ltd., Tokyo, Japan. Anhydrous ethyl alcohol, specially denatured formula 3A, i.e., ethanol denatured with 5 volume percent methanol, is added to the mixture with stirring until a uniformly damp mass formed. The damp mass is extruded through a screen having 20 wires per inch. The extrudate is then allowed to air dry at room temperature overnight. After drying, the resulting extrudate is passed again through a 20-mesh sieve, forming granules. 0.15 Grams of the tableting lubricant, magnesium stearate, is passed through a sieve having 60 wires per inch. The sized 60-mesh lubricant is then tumbled into the granules to produce the finished granulation.

Portions of the resulting granulation are weighed and compacted with caplet-shaped tooling on a Carver press at pressure head of 1.5 tons. Each tablet will contain a target weight of active agent and be of a suitable size to be orally administered. The shape of the tablet may have approximately cylindrical proportions, and the diameter may be approximately 7.5 millimeters (mm) and the length approximately 22 mm.

A tube of polyolefin material having an outside diameter of about 0.1 mm larger than the diameter of the tablet and having a wall thickness of 0.25 mm is sliced with a razor to produce rings. The width of each ring is approximately 3 mm. One ring is then press fitted onto each caplet such that the ring, or band, is located approximately at the midpoint of the length of the caplet. This step completes the fabrication procedure for the dosage form.

Assay

The dosage forms fabricated in Preparation 1 may be placed in a beaker of simulated gastric fluid, as specified in U.S. Pharmacopedia/National Formulary 23/18, having a pH of approximately 1.2 and a maintained temperature of 37° C. to determine release of active agent over time. Additionally, the swollen size of the dosage form may be removed and measured for dimensional change. A swollen device has the general appearance of the dosage form shown in FIG. 2.

EXAMPLE 1

Equivalent amounts of the following polymers may be substituted for the polyethylene oxide in Preparation 1 (all molecular weights are number average molecular weights in grams per mole): hydroxypropyl cellulose (MW: 1,000,000), hydroxypropyl methyl cellulose (MW: 254,000), hydroxyethyl cellulose (MW: 1,300,000), sodium carboxy methylcellulose (MW: 700,000), calcium carboxymethyl cellulose (MW: 700,000), methyl cellulose (MW: 135,000), and polyvinyl alcohol (Elvanol® HV), and dosage forms with a polyethylene band are fabricated to the same dimensions as described in Preparation 1 with equivalent quantities of the active agents acyclovir, ganciclovir, minocycline, metformin and cyclosporin. The prepared dosage forms are retained in the stomach of a dog for a prolonged retention period and deliver the active agents over a prolonged period of time.

EXAMPLE 2

Dosage forms containing equivalent quantities of the active agents of EXAMPLE 2 are prepared according to the procedures in Preparation 1, except that the nonwater soluble hydroattractant used is, respectively, microcrystalline cellulose (Avicel), cross-linked sodium or calcium carboxymethyl cellulose, cellulose fiber (Solka-Floc, Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, and sodium carboxymethyl starch (Expotab, Primojel), sugars and sodium chloride. The prepared dosage forms are retained in the stomach of a subject and deliver active agent over a prolonged period of time.

EXAMPLE 3

The following active agents are substituted, in the quantities indicated in the parentheses following each active agent listed, for the quantity of active agent in Example 1: cimetidine (400 mg; 800 mg, 1200 mg, 1600 mg), ranitidine (150 mg; 200 mg, 300 mg), captopril (12.5 mg; 25 mg; 50 mg; 100 mg, 150 mg), methyldopa (125; 250; 500 mg), and selegiline (5 mg, 10 mg) and the dosage forms are prepared in the same manner as described in Example 1. The prepared dosage forms are retained in the stomach of a subject and deliver active agent over a prolonged period of time.

EXAMPLE 4

Dosage forms of this invention containing metformin are fabricated according to the procedures of Preparation 1, except that the tablet is inserted into a size "00" hard gelatin capsule before banding. The band is applied by a printing process using the methods and compositions described in U.S. Pat. No. 5,534,263, incorporated herein by reference, where the band material is ethyl acrylate/methyl methacrylate 70:30 copolymer (Eudragit NE 30 D, Rohm Tech), formulated with 30% by weight of the plasticizer triacetin. The resulting dosage form is smooth and easy to swallow.

EXAMPLE 5

A gastric platform dosage form for an insoluble drug, metformin free base, is prepared in accordance with the procedures of Preparation 1 by substituting a drug/particle/Polyox mass consisting of 2% metformin base, 38% corn oil, 40% Neusilin and 20% Polyox 303 for the sized active agent-polymer mixture. Then the hydroattractant is added to the mixture and the subsequent steps repeated for this formulation, forming a tableted core.

A solution for use in film coating the tablets is prepared by stirring 40 grams of methyl cellulose (Methocel A15 LV Premium supplied by Dow Chemical, Midland Mich.) and 10 grams of sorbitol 950 grams of purified water at room temperature. The mixture is then chilled overnight at 9°centigrade to complete dissolution. The tablets from above are transferred to a pharmaceutical coating pan spray coated with the solution in a current of warmed air until a dry film coating is deposited onto each tablet.

An aqueous dispersion for use in banding the tablets is prepared by dissolving 30 grams of triacetin in 174.75 grams of ethyl acrylate methylmethacrylate 70:30 copolymer aqueous dispersion (Eudragit® NE40D supplied by Rohm Corporation, Darmstadt, West Germany). Then, 0.1 grams of anti-foam agent (Simethicone Q7-2587, Dow Chemical, Midland, Mich.) is blended into the mixture. This formed the final composition of the banding dispersion.

The film coated tablets from above are then banded by applying a the above banding dispersion in a transfer printing process using a printing wheel having a width of approximately 100 mils (2.54 mm). The banded system is then dried in warm air to remove the water from the aqueous dispersion, leaving a single band located in the center of the caplet having a width of approximately 120 mils (3.05 mm) and a weight of approximately 21 mg. The entire banded system is then overcoated with more of the aqueous-based film coat solution using the formulation and process as described above until a film coat weight of approximately 30 mg is applied. The dosage forms so prepared are retained in the stomach of a dog and deliver active agent over a prolonged period of time.

EXAMPLE 6

The following formulations using calcium hydrogen phosphate are prepared with progesterone as the active agent and formed into tablets using a Carver press.

| Formulation | A | B | C | D | E |
|---|---|---|---|---|---|
| FujiCalin SG | 52% | 52% | 47% | 47% | 44% |
| Cremophor EL | — | 20.6% | 18.6% | 18.6% | 17.6% |
| Cremophor RH | 20.6% | — | — | — | — |
| Myvacet 9-45 | 20.6% | 20.6% | 18.6% | 18.6% | 17.6% |
| Progesterone | 0.84% | 0.84% | 0.76% | 0.76% | 0.72% |
| HPMC E5 | 4.96% | 4.96% | 4.04% | 4.04% | 4.08% |
| PVP XL | — | — | 10% | — | 15% |
| Maltose | — | — | — | 10% | — |
| Mg Stearate | 1% | 1% | 1% | 1% | 1% |

Fujicalin Tablet Preparation

The progesterone, Cremophor and Myvacet are dissolved by combining the materials in a mixing bowl and mixing with a magnetic stir bar in a 40 C. water bath for 3 hours. The resulting solution is slowly added to the FujiCalin granules in a mechanical mixing bowl (KitchenAid mixer) while mixing. Mixing is continued for 10 minutes and the HPMC E5, wet granulated with ethanol, is added. The resulting mass is passed through a 20-mesh screen and allowed to dry overnight under ambient conditions. The dried material is again screened through a 20-mesh screen, and the dried granules are blended with the PVP XL on a roller mixer for 10 minutes. Then, the magnesium stearate is added, and the mixture is blended on the roller mixer for an additional 2 minutes. The resulting material is suitable for tableting. To facilitate release of the tablets from the die components, a small amount of mannitol may be applied to the outside surface of the drug formulation being tableted. Tableting is done on a Carver press at one-quarter ton force.

Figure 5:
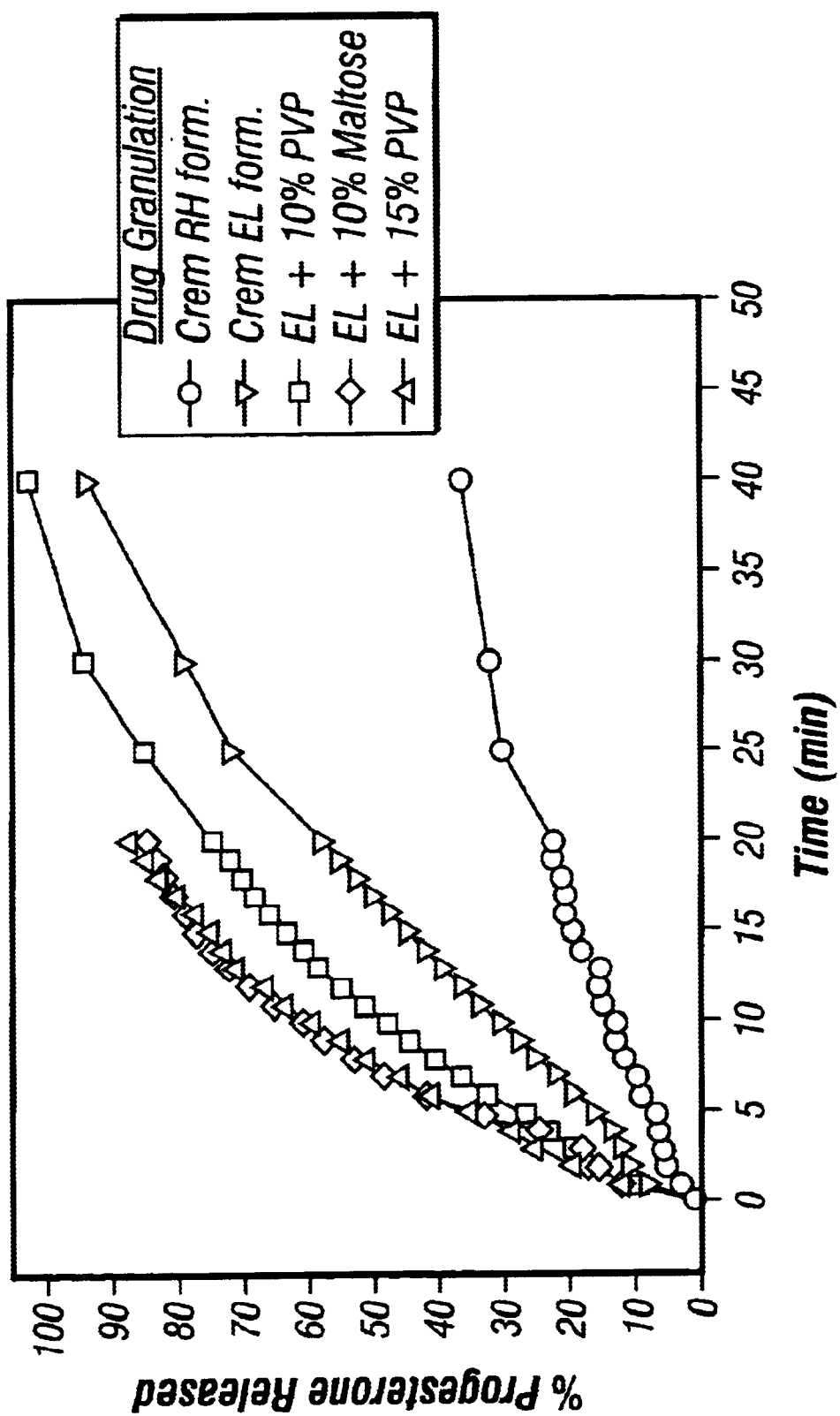
FIG. 5 presents the dissolution profiles in artificial gastric fluid of several different drug layer formulations prepared with calcium hydrogen phosphate as described in Example 6 and illustrates the rapid release of the active agent progesterone from porous calcium hydrogen phosphate particles useful in the practice of the invention.

The dissolution profiles for tablets containing the various drug formulations described above in artificial gastric fluid developed in a USP bath are represented in FIG. 5, in which circles represent formulation A, inverted triangles represent formulation B, squares represent formulation C, diamonds represent formulation D, and triangles represent formulation F. It is apparent from the illustrated results that the active agent progesterone is released into the artificial gastric fluid almost immediately and continues to be released rapidly over a period of minutes. Proportionate amounts of the granular formulations prepared as described above, but without the addition of magnesium stearate and without tableting, are combined with the polyoxyethylene oxide (Polyox 303) as described in Preparation 1 and the corresponding sequential procedures followed as described to produce a finished granulation that is tableted in a cylindrical tablet, approximately 7.5 mm in diameter and approximately 22 mm in length. A tube of polyolefin material is applied as described in Preparation 1 to form finished dosage forms. Those dosage forms can be retained in the stomach of a subject that is administered to and releases liquid, active agent formulation containing progesterone over a prolonged period of time.

EXAMPLE 7

The following formulations using magnesium aluminometasilicate are prepared with progesterone as the active agent and formed into tablets using a Carver press.

Neusilin formulations for drug tablet

| Formulation | G/K | H/L | I/M | J |
|---|---|---|---|---|
| Neusilin US2 | 34% | 36% | 38% | 40% |
| Cremophor EL | 24.99% | 26.46% | 27.93% | 29.4% |
| Myvacet 9-45 | 24.99% | 26.46% | 27.93% | 29.4% |
| Progesterone | 1.02% | 1.08% | 1.14% | 1.2% |
| Ac-Di-Sol or PVP XL | 15% | 10% | 5% | 0% |

Neusilin Tablet Preparation

Figure 6:
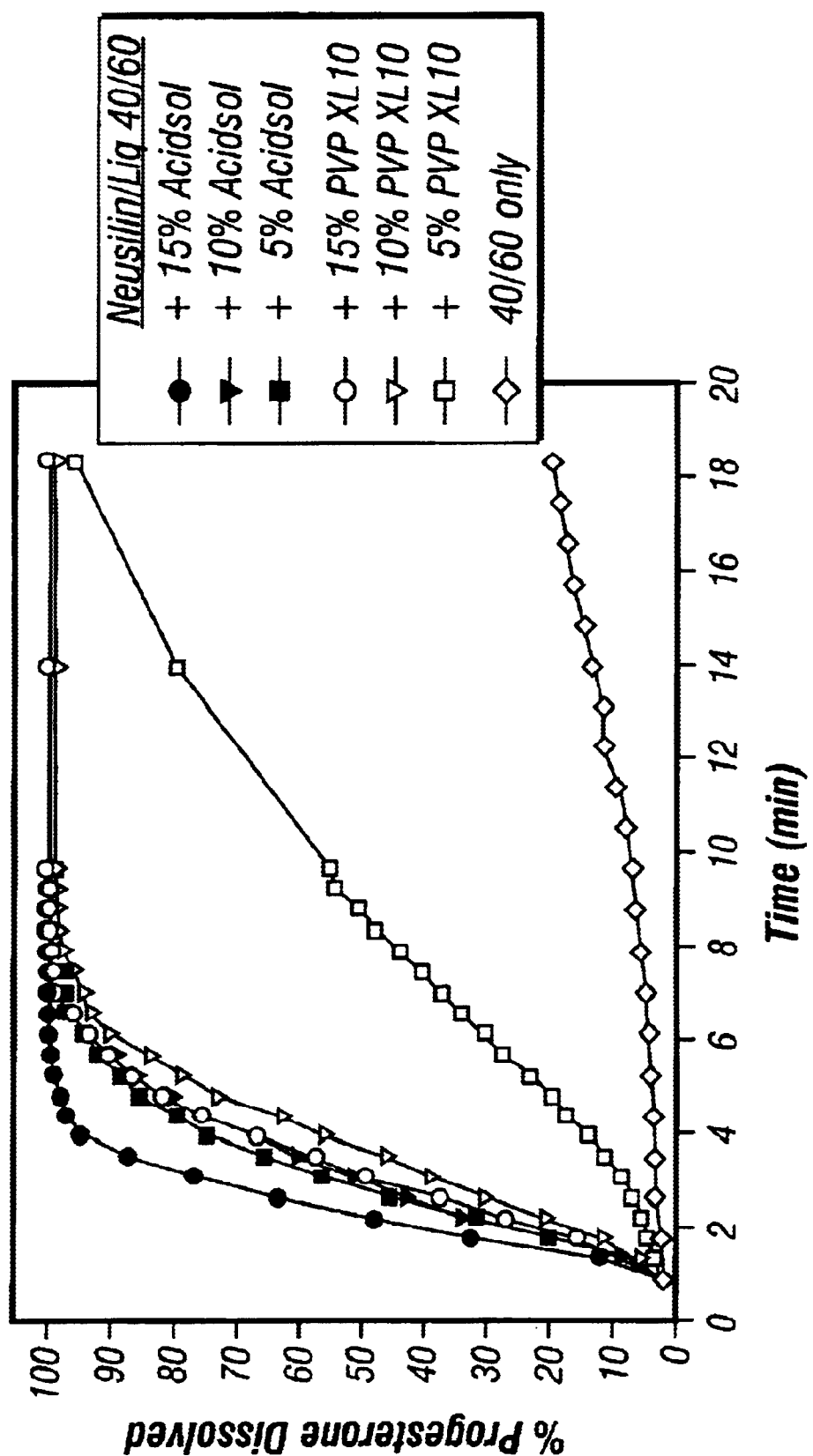
FIG. 6 presents the dissolution profiles in artificial intestinal fluid of several different drug layer formulations prepared with magnesium aluminometasilicate powders as described in Example 7 and illustrates the rapid release of the active agent progesterone from magnesium aluminometasilicate particles useful in the practice of the invention.

Neusilin tablets having formulations as set forth above are prepared in a similar manner to that described for FujiCalin above except that the magnesium stearate and its mixing step are eliminated. Formulations G, H, and I are formed with Ac-Di-Sol. Formulations K, L, and M are formed with PVP XL. Tableting is done on a Carver press at one-quarter ton pressure. Tablets are readily ejected from the die without the use of mannitol. The dissolution profiles for the various formulations are represented in FIG. 6. The filled circles represent formulation G, filled, inverted triangles represent formulation H, and filled squares represent formulation 1. The open circles represent formulation K, open, inverted triangles represent formulation L, and open squares represent formulation M. The filled diamonds represent formulation J. As can be seen therefrom, substantially 100% of the progesterone is dissolved from those tableted formulations that have 10% or more of disintegrant (e.g., Ac-Di-Sol or PVP) in the first 2–6 minutes. Even with only 5% disintegrant present, nearly 100% progesterone is dissolved in the first 20 minutes. This data suggests the desirability of using a small amount of disintegrant with the mangnesium aluminometasilicate powders, which are relatively insoluble in gastric fluid and intestinal fluid, for the most rapid release of active agent. Granulated formulations containing Neuselin US$_2$ particles and progesterone are prepared as described above without tableting, and a proportionate amount of the granular mixture is combined with the polyoxyethylene oxide (Polyox 303) as described in Preparation 1 and the corresponding sequential procedures followed as described to produce a finished granulation that is tableted in a cylindrical tablet, approximately 7.5 mm in diameter and approximately 22 mm in length. A tube of polyolefin material is applied as described in Preparation 1 to form finished dosage forms. Those dosage forms can be retained in the stomach of a subject that is administered to and releases liquid, active agent formulation containing progesterone over a prolonged period of time.

The present invention is described and characterized by one or more of the following technical features and/or characteristics, either alone or in combination with one or more of the other features and characteristics: a dosage form comprising a liquid, active agent formulation absorbed in porous particles, the porous particles being dispersed in a bioerodible carrier, the dosage form being adapted to be retained within the stomach of a subject for a prolonged period of time; a dosage form comprising a liquid, active agent formulation absorbed in porous particles, the porous particles being dispersed in a bioerodible carrier that swells upon imbibing fluid from stomach so as to be retained within the stomach of a subject for a prolonged period of time; a dosage form comprising a liquid, active agent formulation absorbed in porous particles, the porous particles being adapted to resist compaction forces sufficient to form a compacted layer without significant exudation of the liquid, active agent formulation, the particles admixed with a polymer matrix formed of a mixture of a swellable, water soluble polymer that expands when in contact with fluids in the gastric environment and a hydroattractant; a dosage form wherein the matrix is formed with a rigid or semi-rigid segment in which swelling of the matrix is constrained to provide a rigid or semi-rigid section in the dosage form that facilitates the dosage form remaining in the stomach of a subject over a prolonged period of time; a dosage form wherein the liquid, active agent formulation is contained in porous particles having high porosity and having the capacity to absorb at least 5% by weight of the liquid, active agent formulation and resist compressive forces during fabrication of dosage form to minimize exudation of the liquid; a dosage form wherein the rigid or semi-rigid section of the dosage form comprises one or more insoluble materials, having low water permeability and formed as a band circumscribing a portion of the surface of the matrix, that along with the banded portion of the polymer matrix forms the rigid or semi-rigid segment of the dosage form; a dosage form comprising (a) a therapeutically-effective amount of a liquid, active agent formulation sorbed into porous particles, (b) a polymer matrix in which the porous particles are dispersed, the polymer matrix including a high molecular weight, water-soluble polymer and a hydroattractant such as a water-insoluble polymer, and, optionally, non-polymeric water-soluble excipients and polymers of molecular weight of less than 10,000 grams per mole, the polymer matrix having an outer surface for exposure to the environment of use, and (c) a band of insoluble material circumscribing a portion of the outer surface of the polymer matrix; a dosage form adapted for gastric retention and delivery of a liquid, active agent formulation over a prolonged period comprising a polymer matrix formed of a water soluble, high molecular weight polymer and a hydroattractant in which the weight percent of the water soluble, high molecular weight polymer is about 10 to 50 weight percent and the weight percent of the hydroattractant is about 5 to 70 weight percent, and a plurality of porous particles containing the liquid, active agent formulation dispersed throughout the polymer matrix.; a dosage form comprising a unitary compressed dispersion of a liquid, active agent formulation in a plurality of porous particles in a gel-forming, erodible polymer matrix having a first portion that swells in the stomach while maintaining its physical integrity for a prolonged period of time and a second, non-erodible, non-gel-forming portion for promoting retention of the dosage form in the stomach over a prolonged period of time; a dosage form comprising a liquid, active agent formulation absorbed in porous particles, the porous particles being dispersed in a bioerodible carrier adapted to be retained within the stomach of a subject for a prolonged period of time, the porous particles, having a mean particle size of 50–150 microns, being formed by spray drying a scale-like calcium hydrogen phosphate with a specific surface area of 20 $m^2/g$ to 60 $m^2/g$, an apparent specific volume of 1.5 ml/g or more, an oil absorption capacity of 0.7 ml/g or more, a primary particle size of $0.1\mu$ to $5\mu$, and an average particle size of $2\mu$ to $1\mu$ among secondary particles that are aggregates of the primary particles, the scale-like calcium hydrogen phosphate being represented by the following general formula:

$$CaHPO_4 \cdot mH_2O$$

wherein m satisfies the relationship $0 \leq m \leq 0.5$ or $0 \leq m \leq 2.0$; a dosage form comprising a liquid, active agent formulation absorbed in porous particles, the porous particles being dispersed in a bioerodible carrier adapted to be retained within the stomach of a subject for a prolonged period of time, the porous particles being calcium hydrogen phosphate having a specific volume of at least 1.5 ml/g, a BET specific surface area of at least 20 $m^2/g$, and a water absorption capacity of at least 0.7 ml/g; a dosage form comprising a liquid, active agent formulation absorbed in porous particles, the porous particles being dispersed in a bioerodible carrier adapted to be retained within the stomach of a subject for a prolonged period of time, the porous particles being calcium hydrogen phosphate having a specific volume of at least 1.5 ml/g, a BET specific area of at least 20 $m^2/g$, and a water absorption capacity of at least 0.7 ml/g, the particles having a size distribution of 100% less than 40 mesh, 50%–100% less than 100 mesh and 10%–60% less than 200 mesh; a dosage form comprising a liquid, active agent formulation absorbed in porous particles, the porous particles being dispersed in a bioerodible carrier adapted to be retained within the stomach of a subject for a prolonged period of time, the porous particles being calcium hydrogen phosphate having a bulk specific volume of 1.5 ml/g–5 ml/g, a BET specific area of 20 $m^2/g$-60 $m^2/g$, a water absorption capacity of at least 0.7 ml/g, and a mean particle size of 50 microns or greater; a dosage form wherein the number average molecular weight of the water-soluble polymer is between about 100,000 and 20,000,000 grams per mole; a dosage form wherein the water soluble polymer is polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch or polyvinyl alcohol; a dosage form wherein the hydroattractant is low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules or sodium carboxymethyl starch, sugars, and sodium chloride; a dosage form wherein the active agent is an antiviral, antimicrobial, antidiabetic, antihperglycemic, hypoglycemic, antidepressant, antiobesity, immunosuppresive, antiidiabetic or antifungal active agent; a dosage form wherein the active agent is acyclovir, ganciclovir, cimetidine, ranitidine, captopril, methyldopa, selegiline, minocycline, metformin, bupropion, orlistat, cyclosporin, cyclosporine metformin or fexofenadine or a pharmaceutically acceptable salt thereof; a dosage form wherein the active agent is released from the porous particles in a liquid formulation to the gastrointestinal tract over a time period of at least 3 hours; a dosage form adapted for gastric retention comprising a unitary compressed dispersion of a plurality of porous particles having a liquid, active agent formulation sorbed therein in a gel-forming, erodible polymer matrix having a first portion that swells in the stomach while maintaining its physical integrity for a prolonged period of time and a second, non-erodible, non-gel-forming portion for promoting retention of the dosage form in the stomach over a prolonged period of time; a composition comprising from about 1 to 50 weight percent of porous calcium hydrogen phosphate particles having sorbed therein a liquid, active agent formulation, about 5 weight percent to about 50 weight percent of a polyethylene oxide polymer having a number average molecular weight of between about 100,000 and 20,000,000 grams per mole and about 5 weight percent to about 60 weight percent of a hydroxypropyl cellulose polymer having a hydroxypropyl content of between about 10 weight percent and about 13 weight percent of the hydroxypropyl cellulose polymer the porous particles comprising calcium hydrogen phosphate with a specific surface area of 20 m$^2$/g to 60 m$^2$/g, an apparent specific volume of 1.5 ml/g or more, an oil absorption capacity of 0.7 ml/g or more, and a mean particle size of 50 microns or greater, the calcium hydrogen phosphate being represented by the following general formula:

$$CaHPO_4.mH_2O$$

wherein m satisfies the relationship $0 \leq m \leq 0.5$ or $0 \leq m \leq 2.0$; a dosage form comprising a gastric-emptying delaying agent; a dosage form wherein the gastric-emptying delaying agent is selected from anticholonergic agents, methylcellulose, guar gum, fats and fatty acids of 10–15 carbon atoms; a dosage form wherein the proous particle is calcium hydrogen phosphate, microcrystalline cellulose or silicon dioxide; a dosage form wherein the porous particle is magnesium aluminometasilicate represented by the general formula $$Al_2O_3MgO.2SiO_2.nH_2O$$

wherein n satisfies the relationship $0 \leq n \leq 10$; a dosage form wherein the porous particle is magnesium aluminometasilicate represented by the general formula $$Al_2O_3MgO.2SiO_2.nH_2O$$

wherein n satisfies the relationship $0 \leq n \leq 10$ and having a specific surface area of about 100–300 m$^2$/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g, a dosage form wherein the liquid, active agent comprises a pH regulating agent selected from acids or bases.

The above description has been given for ease of understanding only. No unnecessary limitations should be understood therefrom, as modifications will be obvious to those skilled in the art.

What is claimed is:

1. A dosage form comprising:

a bioerodible carrier formulated to facilitate retention of the dosage form within a stomach of a subject and erode over a prolonged period of time as the dosage form is retained in the stomach; and a plurality of porous particles having a liquid active agent formulation absorbed therein, wherein said plurality of porous particles is dispersed within said bioerodible carrier, the porosity of said plurality porous particles is such that liquid active agent formulation comprises at least about 5% and up to about 70% of die weight of the plurality of porous particles said plurality of porous particles is adapted to resist compaction forces sufficient to form a compacted drug layer without significant exudation of the liquid active agent formulation, the dosage form is formulated such that porous particles included in said plurality of porous particles are released from the dosage form as said bioerodible carrier erodes in the stomach; and said liquid active agent formulation is formulated such that 70% or more of an active agent included in said liquid active agent formulation is released from said plurality of porous particles within about 20 minutes from introduction of said porous particles into a fluid environment of use.

2. The dosage form of claim 1, wherein the bioerodible carrier comprises a polymer matrix.

3. The dosage form of claim 1, wherein the plurality of porous particles comprises a calcium hydrogen phosphate represented by the formula $CaHPO_4.mH_2O$, wherein m satisfies the relationship $0 \leq m \leq 2.0$.

4. The dosage form of claim 1, wherein the plurality of porous particles comprises a magnesium aluminonietasilicate represented by the formula $AL_2O_3MgO.2SiO_2.nH_2O$, wherein n satisfies the relationship $0 \leq n \leq 10$.

5. The dosage form of claim 1, wherein said active agent comprises a compound that is absorbed more readily in a portion of the upper gastrointestinal tract of the subject than in any portion of the lower gastrointestinal tract of the subject.

6. The dosage form of claim 1,wherein the plurality porous particles comprises a substantially amorphous material.

7. The dosage form of claim 6, wherein the porosity of said plurality of porous particles is such that the liquid active agent formulation comprises from about 60% to about 70% of the weight of the plurality of porous particles.

8. The dosage form of claim 1, wherein the plurality of porous particles comprises a substantially crystalline material.

9. The dosage form of claim 8, wherein the porosity of said plurality of particles that the liquid active agent formulation comprises from about 30% to of the weight of the plurality of porous particles.

* * * * *